United States Patent [19]

Baichwal et al.

[11] Patent Number: 5,478,574
[45] Date of Patent: Dec. 26, 1995

[54] AGGLOMERATED HYDROPHILIC COMPLEXES WITH MULTI-PHASIC RELEASE CHARACTERISTICS

[75] Inventors: Anand R. Baichwal, Wappingers Falls, N.Y.; John N. Staniforth, Bath, England

[73] Assignee: Edward Mendell Co., Inc., Patterson, N.Y.

[21] Appl. No.: 94,504

[22] Filed: Jul. 20, 1993

Related U.S. Application Data

[63] Continuation-in-part of Ser. No. 922,312, Jul. 30, 1992.
[51] Int. Cl.$^6$ .............................. A61K 9/22; A61K 47/36
[52] U.S. Cl. ........................ 424/485; 424/488; 424/468; 514/964
[58] Field of Search .................... 424/485, 488, 424/468; 514/964

[56] References Cited

U.S. PATENT DOCUMENTS

| | | | |
|---|---|---|---|
| 2,993,836 | 7/1961 | Nash et al. | 167/82 |
| 3,074,852 | 1/1963 | Mayron | 167/82 |
| 3,079,303 | 2/1963 | Raff et al. | 167/82 |
| 3,133,863 | 5/1964 | Tansey | 167/82 |
| 3,147,187 | 9/1964 | Playfair | 167/82 |
| 3,388,041 | 6/1968 | Gans et al. | 167/82 |
| 3,456,049 | 7/1969 | Hotko et al. | 424/22 |
| 3,627,583 | 12/1971 | Troy et al. | 127/29 |

(List continued on next page.)

FOREIGN PATENT DOCUMENTS

| | | | |
|---|---|---|---|
| 0180364 | 7/1986 | European Pat. Off. | |
| 0234670 | 2/1987 | European Pat. Off. | A61K 9/22 |
| 1097207 | 12/1967 | United Kingdom | A61K 3/76 |
| 2178658A | 2/1987 | United Kingdom | A61K 9/22 |
| 2188843 | 10/1987 | United Kingdom | A61K 9/22 |
| 8400104 | 1/1984 | WIPO | A61K 9/24 |
| 8700044 | 1/1987 | WIPO | A61K 9/22 |
| 8705212 | 9/1987 | WIPO | |
| 90003165 | 4/1990 | WIPO | |

OTHER PUBLICATIONS

"Satiaxane Food–Grade Xanthan Gum", a booklet published by Satia.
"Hydrocolloids", a publication by Mero Rousselot Satia, p. 68.
"Xanthan Gum/Keltrol/Keltzan/a Natural Biopolysaccharide for Scientific Water Control", Kelco Division of Merck and Co., Inc., Second Edition, pp. 21–25.
"Formulating for Controlled Release with Methocel Cellulose Ethers", The Dow Chemical Company, ™1987.
Pharm. Ind., vol. 42, No. 6, 1980, Georgakopoulos, et al., "Locust Bean Gum as Granulating and Binding Agent for Tablets".
K. A. Khan, et al., "Pharmaceutical Aspects and In–Vivo Performance of Brufen Retard–an Ibuprofen SR Matrix Tablet", Proceed. Intern. Symp. Control. Rel. Bioact. Mater., 18 (1991), Controlled Release Society, Inc.
P. Giunchedi, et al., "Ketoprofen Pulsatile Absorption from 'Multiple Unit' Hydrophilic Matrices, International Journal of Pharmaceutics", 77 (1991) 177–181.
H. M. Ingani, et al., 6th Pharmaceutical Technology Conference, vol. II, pp. 459–460, Canterbury, England, 1987.
A. C. Shah, et al., "Gel Matrix Systems Exhibiting Bimodal Controlled Release for Oral Drug Delivery", Journal of Controlled Release, 9 (1989) 169–175.
U. Conte, et al., "A New Ibuprofen Pulsed Release Oral Dosage From Drug Development and Industrial Pharmacy", 15 (14–16), 2583–2596 (1989).

*Primary Examiner*—Edward J. Webman
*Attorney, Agent, or Firm*—Steinberg, Raskin & Davidson

[57] ABSTRACT

The present invention relates to a controlled release formulation which includes a therapeutically active medicament, a heterodisperse gum matrix, a pharmaceutically acceptable diluent, and an effective amount of a pharmaceutically acceptable surfactant and/or wetting agent to provide a multi-phasic controlled release of a therapeutically active medicament. The invention also relates to a method of preparing the same.

19 Claims, 9 Drawing Sheets

U.S. PATENT DOCUMENTS

| | | | |
|---|---|---|---|
| 3,629,393 | 12/1971 | Nakamoto et al. | 424/22 |
| 3,639,169 | 2/1972 | Broeg et al. | 127/29 |
| 3,726,690 | 4/1973 | Schuppner, Jr. | 99/139 |
| 3,728,445 | 5/1973 | Bardani | 424/22 |
| 3,773,920 | 11/1973 | Nakamoto et al. | 424/19 |
| 3,836,618 | 9/1974 | Stevens | 264/101 |
| 3,864,469 | 2/1975 | Reiser et al. | 424/22 |
| 3,950,508 | 4/1976 | Mony et al. | 424/19 |
| 3,963,832 | 6/1976 | Hashimoto et al. | 424/56 |
| 4,013,820 | 3/1977 | Farhadieh et al. | 536/64 |
| 4,072,535 | 1/1978 | Short et al. | 106/210 |
| 4,167,558 | 9/1979 | Sheth et al. | 424/22 |
| 4,199,560 | 4/1980 | Gyarmati | 424/19 |
| 4,259,314 | 3/1981 | Lowey | 424/19 |
| 4,308,251 | 12/1981 | Dunn et al. | 424/19 |
| 4,361,545 | 11/1982 | Powell et al. | 424/19 |
| 4,424,235 | 1/1984 | Sheth et al. | 424/319 |
| 4,439,453 | 3/1984 | Vogel | 424/324 |
| 4,525,345 | 6/1985 | Dunn et al. | 424/22 |
| 4,542,011 | 9/1985 | Gleixner | 424/16 |
| 4,556,678 | 12/1985 | Hsiao | 514/652 |
| 4,590,062 | 5/1986 | Jang | 424/19 |
| 4,623,394 | 11/1986 | Nakamura et al. | 106/122 |
| 4,692,337 | 9/1987 | Ukigaya et al. | 424/469 |
| 4,695,463 | 9/1987 | Yang et al. | 424/488 |
| 4,695,467 | 9/1987 | Uemura et al. | 424/502 |
| 4,698,101 | 10/1987 | Koivurinta | 127/30 |
| 4,698,264 | 10/1987 | Steinke | 428/402.2 |
| 4,704,285 | 11/1987 | Alderman | 424/468 |
| 4,717,713 | 1/1988 | Zatz et al. | 514/2 |
| 4,755,389 | 7/1988 | Jones et al. | 424/456 |
| 4,762,702 | 8/1988 | Gergely et al. | 424/300 |
| 4,803,077 | 2/1989 | Mitsuhashi et al. | 424/439 |
| 4,828,836 | 5/1989 | Elger | 424/419 |
| 4,855,143 | 8/1989 | Lowey | 424/468 |
| 4,968,508 | 11/1990 | Oren et al. | 424/468 |
| 5,128,143 | 7/1992 | Baichwal et al. | 424/464 |
| B1 4,389,393 | 10/1985 | Schor et al. | 424/19 |

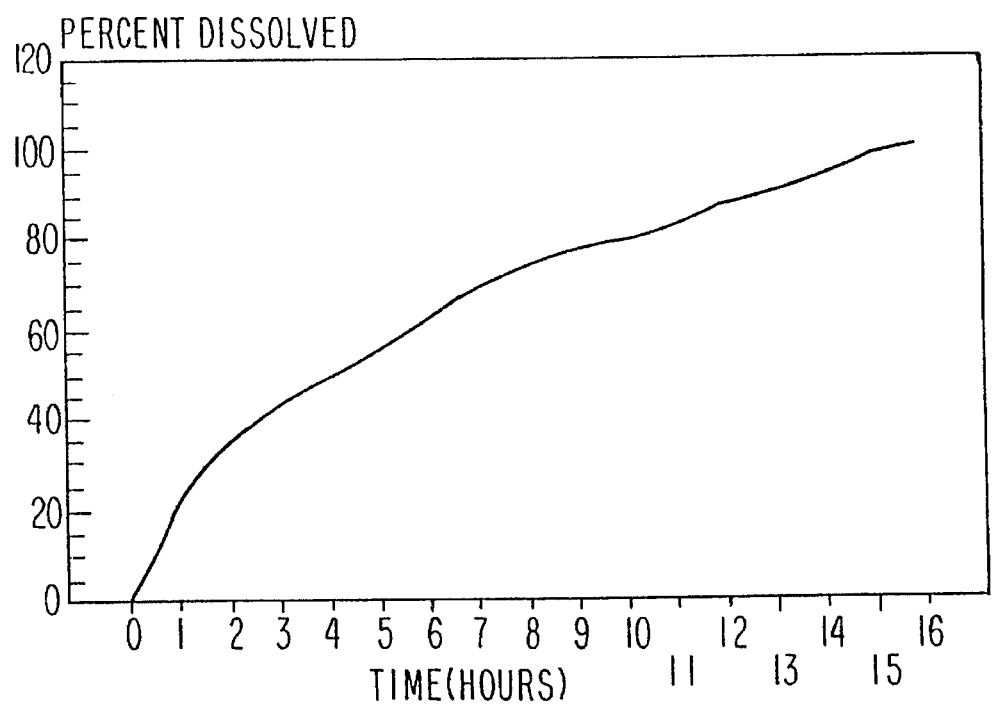
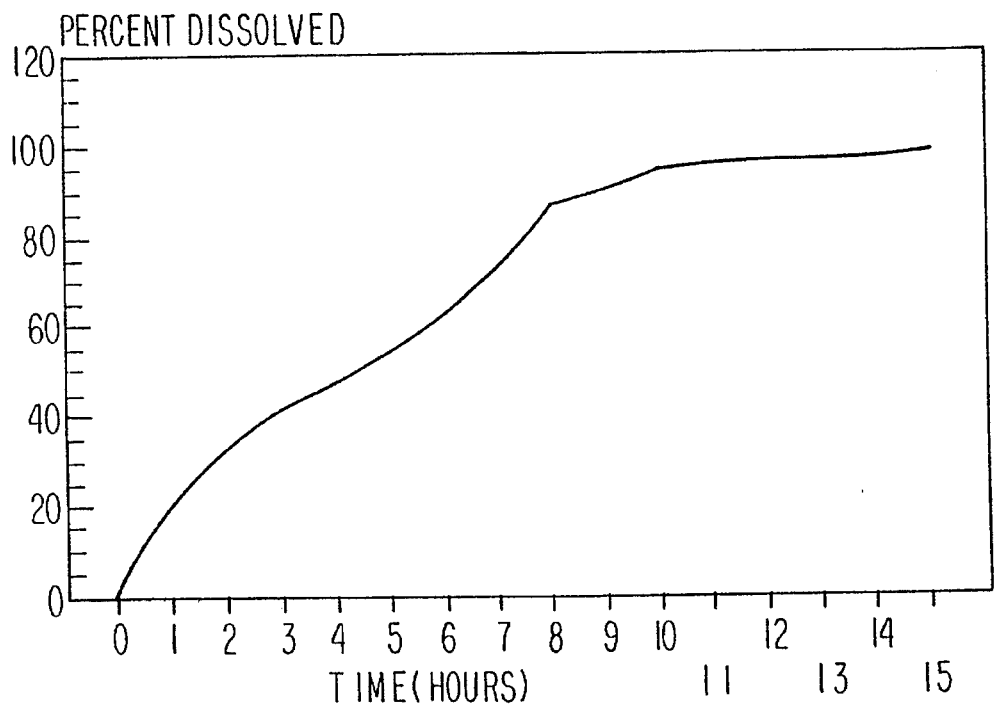

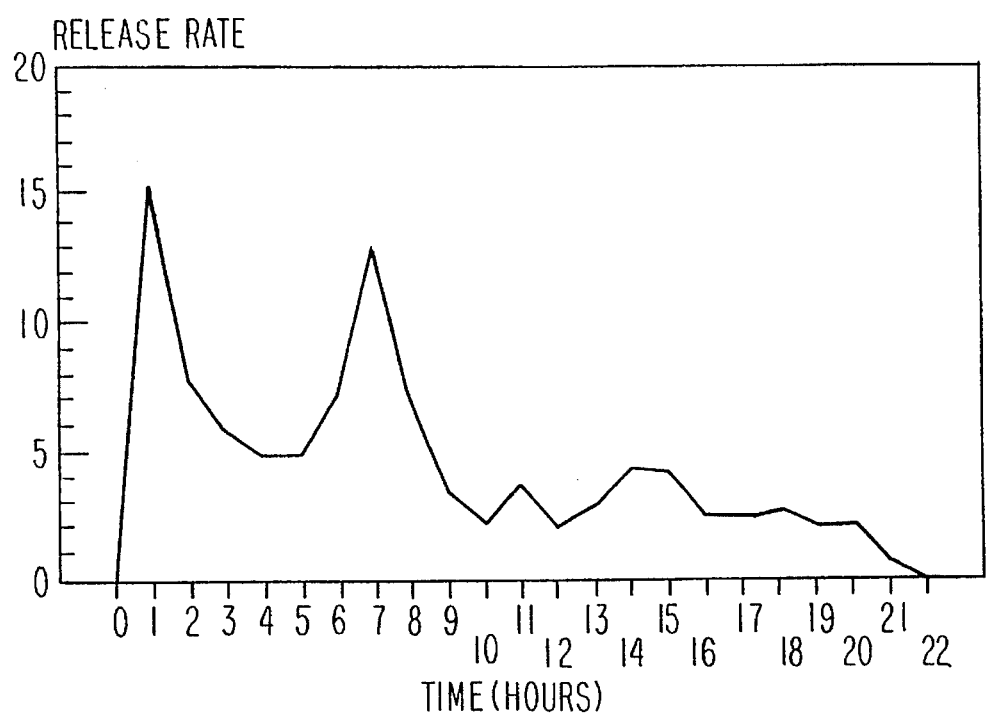
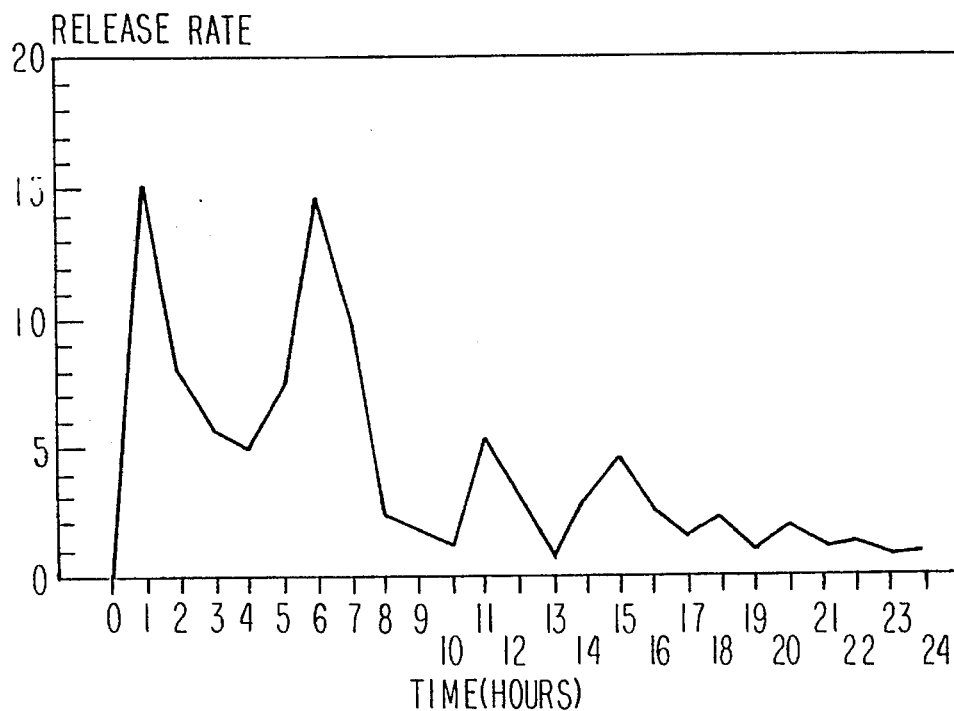

AGGLOMERATED HYDROPHILIC COMPLEXES WITH MULTI-PHASIC RELEASE CHARACTERISTICS

This application is a continuation-in-part application of U.S. Ser. No. 07/922,312, filed Jul. 30, 1992 pending.

BACKGROUND OF THE INVENTION

The advantages of controlled release products are well known in the pharmaceutical field and include the ability to maintain a desired blood level of a medicament over a comparatively longer period of time while increasing patient compliance by reducing the number of administrations necessary to achieve the same. These advantages have been attained by a wide variety of methods. For example, different hydrogels have been described for use in controlled release medicines, some of which are synthetic, but most of which are semi-synthetic or of natural origin. A few contain both synthetic and non-synthetic material. However, some of the systems require special process and production equipment, and in addition some of these systems are susceptible to variable drug release.

Oral controlled release delivery systems should ideally be adaptable so that release rates and profiles can be matched to physiological and chronotherapeutic requirements.

For the most part, the release rate of oral delivery systems have been classified according to the mechanism of release, such as zero order, first order, second order, pseudo-first order, etc., although many pharmaceutical compounds release medicament via other, complicated mechanisms.

First order mechanisms refer to situations where the reaction rate is dependent on the concentration of the reacting substance (and therefore is dependent on the first power of the reactant). In such mechanisms, the substance decomposes directly into one or more products.

Second order mechanisms occur when the experimentally determined rate of reaction is proportional to the concentration of each of two reactants, or to the second power of the concentration of one reactant.

Pseudo first order reactions are generally defined as second order reactions which behave as though they are governed by a first order mechanism, and occur, for example, when the amount of one reacting material is manipulated by being present in great excess or being maintained at a constant concentration as compared to the other substance. In such circumstances, the reaction rate is determined by the manipulated substance.

Zero order mechanisms refer to situations where the reaction rate is independent of the concentration of the reacting substance (and therefore is dependent on the zero power of the reactant), the limiting factor being something other than the concentration of the reacting substance (e.g., the medicament). The limiting factor in a zero order mechanism may be, for example, the solubility of the reacting substance or the light intensity in photochemical reactions.

As previously mentioned, however, many chemical reactions are not simple reactions of zero-, first-, or second-order, etc., and instead comprise a combination of two or more reactions.

Moreover, other factors may influence the reaction rate, including temperature, pH, food effect variability, ions and ionic strength dependency, viscosity dependency, corrosion/erosion variability, content uniformity problems, flow and weight uniformity problems, carrying capacity and mechanical strength problems, hydrolysis, photochemical decomposition, interaction between components (such as interactions between the drug and other ingredients in the formulation, such as buffers, preservatives, etc.), the concentration of solvents of low dielectric constant (when the reaction involves oppositely charged ions), etc.

Generally, controlled release pharmaceutical formulations which provide zero order release characteristics have been considered most desirable because such a mechanism would theoretically provide constant drug levels. This is based on the assumption that the rate of elimination is determinative of the release rate of the medicament from the formulation, rather than the rate of absorption, etc.

However, for medicaments which are not very soluble in the stomach and where absorption is desired for a prolonged period of time, a bimodal release mechanism is considered to be desirable.

Bimodal or multi-phasic release is characterized by an initial high rate followed by a slower rate as the dosage form passes the upper portion of the small intestine where absorption is maximum and finally another higher rate as the dosage form passes into the further end of the intestine where absorption is less than before.

Bimodal release is considered to be advantageous for a number of reasons, including but not limited to the fact that bimodal release allows the formulator to compensate for changing absorption rates of the medicament in the gastrointestinal tract by providing a rapid onset of action (when the formulation is located in the stomach) and compensate for relatively slow absorption by providing a relatively rapid release rate (e.g., when the formulation is located in the large intestine).

Bimodal release formulations have been provided in a number of different manners to date.

For example, International Publication Number WO/87/00044 describes therapeutic formulations which are said to have bimodal release characteristics. WO 87/00044 describes a carrier base material for therapeutically active medicaments in a solid dosage formulation that are said to produce a bimodal controlled release profile characterized by a rapid initial release of medicament followed by a substantially constant rate of release for a period of time, after which the release rate is greater than the constant rate previously observed. The carrier based material comprises bimodal hydroxypropylmethylcellulose ethers with a methoxy content of 19–30%, a hydroxy propoxy content of 4–12%, a viscosity of 40–19,000 cps, an average molecular weight of 20,000–140,000, and which demonstrates a bimodal release profile in accordance with an assay method described therein. The bimodal hydroxypropymethylcelluloses comprise 5–99% by weight of the total formulation, depending upon the active ingredient and length of drug released desire.

A. C. Shah et al., "Gel-Matrix Systems Exhibiting Bimodal Controlled Release For Oral Drug Delivery", Journal of Controlled Release, 9(1989), pp. 169–175, further reported that certain "types" of hydroxypropylmethylcellulose ethers are found to display a bimodal drug release profile. However, in that study, series of hydroxypropylmethylcellulose ether polymers were found to provide bimodal and non-bimodal release profiles from polymer-drug matrix tablets, which results appeared to depend upon the supplier of the polymer (and therefore upon, e.g., the method of manufacture, ionic composition, variations in the distribution of substituent groups, or distribution of molecular weight fractions).

P. Giunchedi et al., "Ketoprofen Pulsatile Absorption From 'Multiple Unit' Hydrophilic Matrices", International Journal of Pharmaceutics, 77(1991), pp. 177–181 described an extended release oral formulation of Ketoprofen comprising a multiple unit formulation constituted by four hydrophilic matrices of identical composition, each containing 50 mg of drug and prepared with hydroxypropylmethylcellulose (Methocel®) and placed in a gelatin capsule. Pulsatile plasma levels (2 peaks at 2nd and 8th hours after dosing) were said to be obtained, whereas in vitro tests resulted in a fairly constant drug release.

U. Conte et al., "A New Ibuprofen Pulsed Release Oral Dosage Form", Drug Development And Industrial Pharmacy, 15(14–16), pp. 2583–2596 (1989) reported that a pulsed released pattern was obtained from a 3-layer tablet wherein two layers contained a dose of drug, and an intermediate layer acted as a control element separating the drug layers. The control element was a mixture of water-swellable polymers (hydroxypropylmethylcelluloses). An outer film of an impermeable polymer coated the tablet. A superdisintegrant (sodium starch glycolate and cross-linked polyvinyl pyrrolidone) was included in the drug layers.

K. A. Kahn et al, "Pharmaceutical Aspects And In-Vivo Performance Of Brufen Retard—An Ibuprofen SR Matrix Tablet", Proced. Intern. Symp. Control. Rel. Bioact. Mater., 18(1991), Controlled Release Society, Inc., describes a formulation containing 800 mg of ibuprofen which is said to provide a bimodal release pattern. The release retarding agent utilized therein was xanthan gum. The ingredients were blended to the appropriate xanthan gum content, and thereafter compressed into tablets and film coated. The amount of xanthan gum included inversely affected the rate of drug release. An increase in drug particle size or quantity of film-coat per tablet did not significantly effect the rate of drug release. Although an increase in particle size of the xanthan gum caused a more pronounced burst effect, the application of the film-coat overcame this burst effect. The rapid initial release of the medicament was hypothesized to be related to changes in the formation of the gel layer, wherein larger particles gel more slowly and are sloughed off before a coherent matrix can form.

In our U.S. Pat. Nos. 4,994,276, 5,128,143, and 5,135,757, hereby incorporated by reference, we reported that a controlled release excipient which is comprised of synergistic heterodisperse polysaccharides (e.g., a heteropolysaccharide such as xanthan gum in combination with a polysaccharide gum capable of cross-linking with the heteropolysaccharide, such as locust bean gum) is capable of processing into oral solid dosage forms using either direct compression, following addition of drug and lubricant powder, conventional wet granulation, or a combination of the two. The release of the medicament from the formulations therein proceeded according to zero-order or first-order mechanisms.

The controlled release excipients disclosed in U.S. Pat. Nos. 4,994,276, 5,128,143, and 5,135,757 are commercially available under the tradename TIMERx™ from Edward Mendell Co., Inc., Patterson, N.Y., which is the assignee of the present invention.

OBJECTS AND SUMMARY OF THE INVENTION

It is therefore an object of the present invention to provide a formulation capable of providing multi-phasic or bi-phasic controlled release of a therapeutically active medicament.

It is a further object of the present invention to provide a means of converting the mechanism of drug release provided by formulations comprising the excipient described in U.S. Pat. Nos. 4,994,276, 5,128,143, and 5,135,757 from zero-order or first-order to a bi-phasic or multi-phasic mechanism.

It is a further object of the present invention to provide a controlled release multi-phasic excipient which can be mixed with a medicament and tableted to thereby provide a multi-phasic release of the active agent when the tablet is exposed to aqueous fluids, gastro-intestinal fluids, etc.

It is a further object of the present invention to provide a controlled release tablet which releases a therapeutically active medicament according to bi- or multi-phasic kinetics.

The above-mentioned objects and others are achieved by virtue of the present invention, which relates in part to a controlled release formulation comprising a controlled release excipient comprising a heterodisperse polysaccharide component and a saccharide component; a further component comprising a surfactant and/or a wetting agent; and a therapeutically active medicament. More particularly, it has now been surprisingly discovered that combination of pharmaceutically acceptible surfactants and/or wetting agents in the controlled release excipients disclosed in U.S. Pat. Nos. 4,994,276, 5,128,143, and 5,135,757 can be used to trigger changes in release patterns and produce bi- or multi-phasic profiles of the final formulation, possibly via further changes in cross-linking, gel strength and gel-sol transitions.

The present invention further relates to a controlled release oral solid dosage form, comprising a heterodisperse material comprising a heteropolysaccharide gum and a homopolysaccharide gum capable of cross-linking said heteropolysaccharide gum in the presence of aqueous solutions, the ratio of said heteropolysaccharide gum to said homopolysaccharide gum being from about 1:3 to about 3:1; an inert pharmaceutical diluent selected from the group consisting of monosaccharide, a disaccharide, a polyhydric alcohol, and mixtures thereof, the ratio of said inert diluent to said heterodisperse material being from about 3:7 to about 7:3; and an effective amount of a pharmaceutically acceptable surfactant or wetting agent to provide a multi-phasic release of a therapeutically active agent. In a preferred embodiment, the formulation of the present invention comprises a tablet.

The present invention further relates to a method for preparing an oral solid dose formulation providing a multi-phasic release of a therapeutically active medicament when said dosage form is exposed to aqueous or gastric fluid. In the method, a heteropolysaccharide gum is mixed with a homopolysaccharide gum capable of cross-linking said heteropolysaccharide gum in the presence of aqueous solutions, such that the ratio of said heteropolysaccharide gum to said homopolysaccharide gum is from about 1:3 to about 3:1, to obtain a heterodisperse gum matrix. An inert pharmaceutical diluent is added to said heterodisperse gum matrix such that the ratio of the inert diluent to said heterodisperse gum matrix is from about 3:7 to about 7:3. An effective amount of a medicament is added to render a therapeutic effect. An effective amount of a pharmaceutically acceptable surfactant or wetting agent is added to provide a multi-phasic release of said medicament when the dosage form is exposed to aqueous fluid.

The present invention is further related to a controlled release multi-phasic pharmaceutical excipient comprising a heterodisperse gum matrix comprising a heteropolysaccharide gum and a homopolysaccharide gum capable of cross-linking the heteropolysaccharide gum in the presence of aqueous solutions, an inert pharmaceutical diluent selected from the group consisting of monosaccharide, a disaccharide, a polyhydric alcohol, and mixtures thereof, and from about 1 to about 20 percent by weight of a pharmaceutically acceptable surfactant or wetting agent. The ratio of heteropolysaccharide gum to homopolysaccharide gum, as well as the ratio of inert diluent to heterodisperse gum matrix in the controlled release multi-phasic excipient is as set forth above with respect to the final formulation.

The present invention further relates to a method for preparing a controlled release dosage form which exhibits multi-phasic release of a medicament incorporated therein, comprising preparing a controlled release multi-phasic excipient as described above, and incorporating a therapeutically effective amount of a medicament along with any pharmaceutically necessary additives such as a lubricant, and tableting the mixture.

BRIEF DESCRIPTION OF THE DRAWINGS

The following drawings are illustrative of embodiments of the invention and are not meant to limit the scope of the invention as encompassed by the claims.

FIG. 1 is a graphical representation of the dissolution curve (expressed as percent dissolved over time) provided by the tablets of Example 2 (no surfactant);

FIGS. 2–9 are graphical representations of the dissolution curves (expressed as percent dissolved over time) provided by the tablets of Examples 3–10 (surfactant(s) included);

FIGS. 11–18 are graphical representations of the dissolution curves (expressed as release rate over time) provided by the tablets of Examples 3–10 (surfactant(s) included).

DETAILED DESCRIPTION

Figure 3:
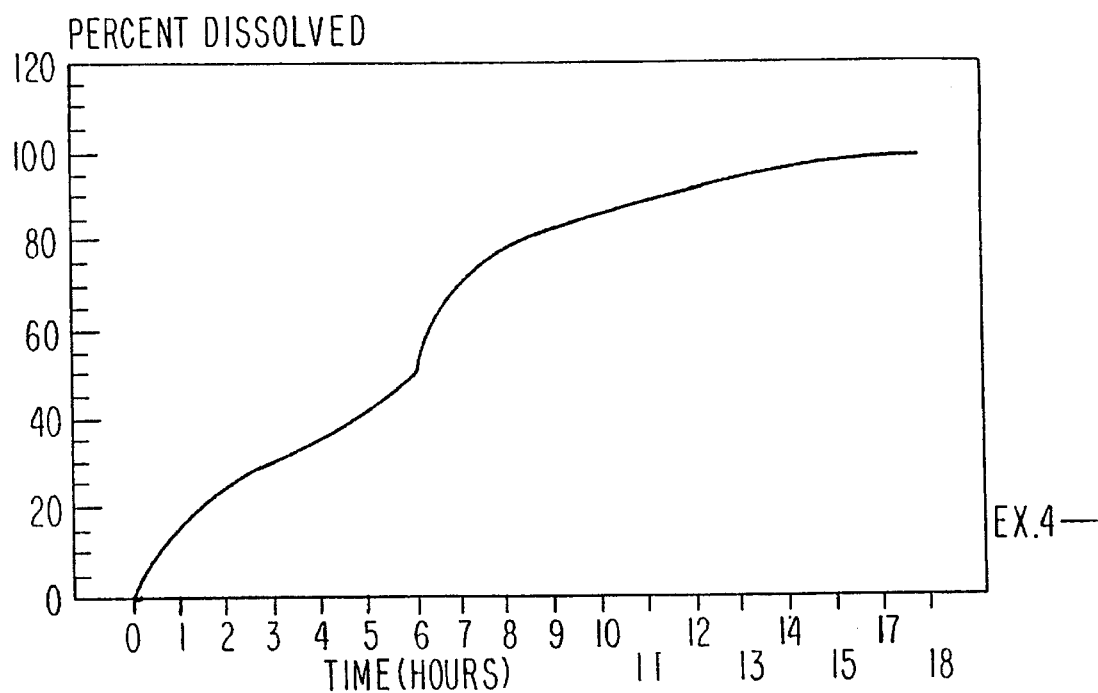

The term "heteropolysaccharide" as used in the present invention is defined as a water-soluble polysaccharide containing two or more kinds of sugar units, the heteropolysaccharide having a branched or helical configuration, and having excellent water-wicking properties and immense thickening properties. When admixed with an appropriate homopolysaccharide gum capable of cross-linking with the heteropolysaccharide in accordance with the present invention and exposed to an aqueous solution, gastric fluid, etc., the gums pack closely and many intermolecular attachments are formed which make the structure strong and provide a hydrophilic gum matrix having high gel strength.

Xanthan gum, the preferred heteropolysaccharide, is produced by microorganisms, for instance, by fermentation with the organism xanthomonas compestris. Most preferred is xanthan gum which is a high molecular weight (>$10^6$) heteropolysaccharide. Xanthan gum contains D-glucose, D-mannose, D-glucuronate in the molar ratio of 2.8:2.0:20, and is partially acetylated with about 4.7% acetyl. Xanthan gum also includes about 3% pyruvate, which is attached to a single unit D-glucopyromosyl side chain as a metal. It dissolves in hot or cold water and the viscosity of aqueous solutions of xanthan gum is only slightly affected by changes in the pH of a solution between 1 and 11.

Other preferred heteropolysaccharides include derivatives of xanthan gum, such as deacylated xanthan gum, the carboxymethyl ether, and the propylene glycol ester.

The homopolysaccharide gums used in the present invention which are capable of cross-linking with the heteropolysaccharide include the galactomannans, i.e., polysaccharides which are composed solely of mannose and galactose.

A possible mechanism for the interaction between the galactomannan and the heteropolysaccharide involves the interaction between the helical regions of the heteropolysaccharide and the unsubstituted mannose regions of the galactomannan. Galactomannans which have higher proportions of unsubstituted mannose regions have been found to achieve more interaction with the heteropolysaccharide. Hence, locust bean gum, which has a higher ratio of mannose to the galactose, is especially preferred as compared to other galactomannans such as guar and hydroxypropyl guar.

The inert filler of the excipient preferably comprises a pharmaceutically acceptable saccharide, including a monosaccharide, a disaccharide, and/or mixtures thereof. Examples of suitable inert pharmaceutical fillers include sucrose, dextrose, lactose, microcrystalline cellulose, fructose, xylitol, sorbitol, mixtures thereof and the like. However, it is preferred that a soluble pharmaceutical filler such as lactose, dextrose, sucrose, or mixtures thereof be used.

The excipient of the present invention has uniform packing characteristics over a range of different particle size distributions and is capable of processing into tablets using either direct compression, following addition of drug and lubricant powder or conventional wet granulation.

The properties and characteristics of a specific excipient system prepared according to the present invention is dependent in part on the individual characteristics of the homo and hetero polysaccharide constituents, in terms of polymer solubility, glass transition temperatures etc., as well as on the synergism both between different homo and heteropolysaccharides and between the homo and heteropolysaccharides and the inert saccharide constituent(s) in modifying dissolution fluid-excipient interactions.

A homodisperse system of a heteropolysaccharide typically produces a highly ordered, helical or double helical molecular conformation which provides high viscosity without gel formation. In contrast, a homodisperse system of a homopolysaccharide typically is only slowly soluble and ungelled at low temperatures. Two steps which are generally required for gelation are the fast hydration of the macromolecules which comprise the hydrodisperse polysaccharide material and thereafter the association of the molecules to form gels. These two important properties which are necessary to achieve a slow release hydrophilic matrix are maximized in the present invention by the particular combination of materials. Prolonged exposure to the dissolution fluid promotes solubilization, which allows molecules to associate and undergo gelation, and may result in inter-macromolecular cross-linking in ribbon or helical "smooth" regions.

The heterodisperse excipient of the present invention comprises both hetero- and homo- polysaccharides which exhibit synergism. The heteropolysaccharide component acts to produce a faster gelation of the homopolysaccharide component and the homopolysaccharide acts to cross-link the normally free heteropolysaccharide helices. The resultant gel is faster-forming and more rigid. Heteropolysaccharides such as xanthan gum have excellent water wicking properties which provide fast hydration. On the other hand, the combination of xanthan gum with homopolysaccharide gums which are capable of cross-linking the rigid helical ordered structure of the xanthan gum (i.e. with unsubstituted mannose regions in the galactomannans) thereby act synergistically to provide a higher than expected viscosity (i.e., high gel strength) of the matrix. The combination of xanthan gum with locust bean gum with or without the other homopolysaccharide gums is especially preferred. However, the combination of any homopolysaccharide gums known to produce a synergistic effect when exposed to aqueous solutions may be used in accordance with the present invention. By synergistic effect, it is meant that the combination of two or more polysaccharide gums produce a higher viscosity and/or faster hydration than that which would be expected by either of the gums alone.

It is also possible that the type of synergism which is present with regard to the gum combination of the present invention could also occur between two homogeneous or two heteropolysaccharides.

In the present invention, it has been discovered that the controlled release properties of the tablets are optimized when the ratio of heteropolysaccharide gum to homopolysaccharide material is about 1:1, although heteropolysaccharide gum in an amount of from about 20 to about 80 percent or more by weight of the heterodisperse polysaccharide material provides an acceptable slow release product.

The mixed individual and synergistic viscosity modifying and gel-forming characteristics of the excipient system of the present invention produce a variety of possible release-controlling mechanisms in any given excipient system. Some of this behavior has been described by an equation such as that reported for example by Frisch, "Sorption and Transport in Glassy Polymers—A Review", Polymer Eng. Sci. 20 (1980), pp. 2–13, Fan & Singh, "Controlled Release: A Quantitative Treatment", published by Springer Verlag, Berlin and London (1989), pp; 111–156; and Korsmeyer et al., "Mechanisms of Solute Release from Porous Hydrophilic Polymers", Int. H. Pharm. 15 (1983), pp. 25–35:

$$\frac{Mt}{M\infty} = kt^n$$

Where:

$$\frac{Mt}{M\infty}$$

is the fractional solvent absorbed or drug released; t is the solvent absorption or drug release time; k and n are kinetic constants which depend on and can be used to characterize the mechanism of solvent sorption or drug release.

The mechanisms of solvent sorption and drug release vary from Case I or Fickian diffusion (n=0.5, k=diffusion coefficient in initial half of solvent sorption (drug release); to Case II (n=1.0, k∝constant velocity of gel-glassy polymer interface); Super Case II (n>1 probably with Fickian tailing ahead of slow Case II interface velocity) causing accelerated solvent sorption and drug release when the solvent fronts meet at the three dimensional centroid; and Anomalous Behavior (0.5<n< 1), k is a characteristic of solvent/drug solution diffusion and polymer relaxation.

In some cases, modulated drug release profiles are not well fitted to this model and require a more complex function, which takes into account a specific time at which the mechanism changes from one type to another, as the result of a time-dependent trigger for an excipient/excipient, excipient/fluid, drug/fluid, excipient/drug or mixed interaction. This may take the form of a power series such as:

$$\frac{Mt}{M\infty} = k_1 t_1^{n1} + k_2 t_2^{n2}$$

Alternatively, one skilled in the art will recognize that some other function may more accurately model this complex behavior.

The rate-limiting step for the dissolution of tablets of the present invention is believed to be dependent to a large extent upon the penetration of water (or gastric fluid) into the tablet to dissolve the polysaccharides and the drug(s). It is further believed that the presence of the surfactant in the formulation allows faster initial penetration of fluid and an initial "burst" of drug release from the formulation. A second burst of drug release may then occur due to the further action of the surfactant, as the fluid front from one side of the tablet meets the fluid front on the opposite side. The above hypotheses are included for discussion purposes only and are not intended to limit the scope of the present invention.

The chemistry of certain of the ingredients comprising the excipients of the present invention such as xanthan gum is such that the excipients are considered to be self-buffering agents which are substantially insensitive to the solubility of the medicament and likewise insensitive to the pH changes along the length of the gastrointestinal tract.

The final formulation of the present invention comprises a sufficient amount of surfactant or wetting agent to provide a multi-phasic release of the drug(s). In certain preferred embodiments, the surfactant or wetting agent comprises from about 1 to about 10 of the final formulation, by weight. However, the upper limit of the amount of surfactant or wetting agent included in the formulations of the present invention may be higher than 10%; the limiting concern being that the final product should provide a pharmaceutically acceptable formulation. For example, in the case of tablets, the upper limit of the amount of surfactant or wetting agent included is determined by the production of a pharmaceutically acceptable tablet, e.g., a tablet which has a friability of less than about 1% and a hardness of 6–8 kg.

The surfactants which may be used in the present invention generally include pharmaceutically acceptable anionic surfactants, cationic surfactants, amphoteric (amphipathic/amphophilic) surfactants, and non-ionic surfactants. Suitable pharmaceutically acceptable anionic surfactants include, for example, monovalent alkyl carboxylates, acyl lactylates, alkyl ether carboxylates, N-acyl sarcosinates, polyvalent alkyl carbonates, N-acyl glutamates, fatty acid-polypeptide condensates, sulfuric acid esters, alkyl sulfates (including sodium lauryl sulfate (SLS)), ethoxylated alkyl sulfates, ester linked sulfonates (including docusate sodium or dioctyl sodium succinate (DSS)), alpha olefin sulfonates, and phosphated ethoxylated alcohols.

Suitable pharmaceutically acceptable cationic surfactants include, for example, monoalkyl quaternary ammonium salts, dialkyl quaternary ammonium compounds, amidoamines, and aminimides.

Suitable pharmaceutically acceptable amphoteric (amphipathic/amphophilic) surfactants, include, for example, N-substituted alkyl amides, N-alkyl betaines, sulfobetaines, and N-alkyl β-aminoproprionates.

Suitable pharmaceutically acceptable wetting (solubilizing) agents, include pharmaceutically acceptable non-ionic surfactants such as, for example, polyoxyethylene compounds, ethoxylated alcohols, ethoxylated esters, ethoxylated amides, polyoxypropylene compounds, propoxylated alcohols, ethoxylated/propoxylated block polymers, and propoxylated esters, alkanolamides, amine oxides, fatty acid esters of polyhydric alcohols, ethylene glycol esters, diethylene glycol esters, propylene glycol esters, glyceryl esters, polyglyceryl fatty acid esters, sorbitan esters, sucrose esters, and glucose (dextrose) esters.

Other suitable pharmaceutically acceptable wetting (solubilizing) agents include acacia, benzalkonium chloride, cholesterol, emulsifying wax, docusate sodium, glyceryl monostearate, lanolin alcohols, lecithin, poloxamer, poloxyethylene castor oil derivatives, poloxyethylene sorbitan fatty acid esters, poloxyethylene stearates, sodium lauryl sulfates, sorbitan esters, stearic acid, and triethanolamine.

Mixed surfactant/wetting agent systems are also useful in conjunction with the present invention. Examples of such mixed systems include, for example, sodium lauryl sulfate/ polyethylene glycol (PEG) 6000 and sodium lauryl sulfate/ PEG 6000/stearic acid.

The change in the mechanism of drug release from the excipients of the present invention from mono-phasic to bi- or multi-phasic release may further be altered or enhanced by process changes during the manufacture of the excipient, or by formulation alteration. Further modifications in bi- or multi-phasic release profiles can be effected by addition of synergism-modifying components. For example, this can occur as a result of selection of interacting polysaccharides in which the synergism is potentiated by ionic strength of pH. In addition, the saccharide component may also be changed, although the effect of different saccharides on drug release is much smaller than that of different polysaccharides, but may still be important in achieving fine control of drug release. The dissolution profiles of a tablet formulation containing an excipient system with a given heterodisperse polysaccharide component can also be modified by alteration of the ratios of heteropolysaccharide to homopolysaccharide. Alternatively or additionally, the drug release profiles can also be controlled by changing the ratio of heterodisperse polysaccharides to saccharides in the excipient system.

Delays in the onset of mono or multi-phasic release, which may be desirable in order to optimize colonic absorption, can be produced through changes in core formulation or by application of tablet coatings to further modify drug release patterns.

In addition to the inclusion of surfactants/wetting agents, the drug release mechanism of the controlled release excipient of the present invention may be further manipulated by altering the process utilized for tableting i.e. direct compression v/s wet granulation v/s combination of both, and via changes in the formulation itself (i.e., changes in the ratio of heterodisperse polysaccharide to insert saccharide, etc.).

An effective amount of any generally accepted pharmaceutical lubricant, including the calcium or magnesium soaps may be added to the above-mentioned ingredients of the excipient be added at the time the medicament is added, or in any event prior to compression into a said dosage form. Most preferred is magnesium stearate in any amount of about 0.5–3% by weight of the solid dosage form.

The combination of the heterodisperse polysaccharide material (i.e., a mixture of xanthan gum and locust beam gum) with the inert saccharide diluent provides a ready-to-use product in which a formulator need only blend the desired active medicament and an optional lubricant with the excipient and then compress the mixture to form slow release tablets. The excipient may comprise a physical admix of the gums along with a soluble excipient such as compressible sucrose, lactose or dextrose, although it is preferred to granulate or agglomerate the gums with plain (i.e., crystalline) sucrose, lactose, dextrose, etc., to form an excipient. The granulate form has certain advantages including the fact that it can be optimized for flow and compressibility; it can be tableted, formulated in a capsule, extruded and spheronized with an active medicament to form pellets, etc.

The pharmaceutical excipients prepared in accordance with the present invention may be prepared according to any agglomeration technique to yield an acceptable excipient product. In wet granulation techniques, the desired amounts of the heterpolysaccharide gum, the homopolysaccharide gum, and the inert saccharide diluent are mixed together and thereafter a moistening agent such as water, propylene glycol, glycerol, alcohol or the like is added to prepare a moistened mass. Next, the moistened mass is dried. The dried mass is then milled with conventional equipment into granules. Therefore, the excipient product is ready to use.

The excipient is free-flowing and directly compressible. Accordingly, the excipient may be mixed in the desired proportion with a therapeutically active medicament and optional lubricant (dry granulation). Alternatively, all or part of the excipient may be subjected to a wet granulation with the active ingredient and thereafter tableted. The complete mixture, in an amount sufficient to make a uniform batch of tablets, is then subjected to tableting in a conventional production scale tableting machine at normal compression pressure, i.e. about 2000–1600 lbs/sq in. However, the mixture should not be compressed to such a degree that there is subsequent difficulty in its hydration when exposed to gastric fluid.

One of the limitations of direct compression as a method of tablet manufacture is the size of the tablet. If the amount of active is high a pharmaceutical formulator may choose to wet granulate the active with other excipients to attain a decent size tablet with the right compact strength. Usually the amount of filler/binder or excipients needed in wet granulation is less than that in direct compression since the process of wet granulation contributes to some extent toward the desired physical properties of a tablet.

The average tablet size for round tablets is preferably about 500 mg to 750 mg and for capsule-shaped tablets about 750 mg to 1000 mg.

The average particle size of the granulated excipient of the present invention ranges from about 50 microns to about 400 microns and preferably from about 185 microns to about 265 microns. The particle size of the granulation is not narrowly critical, the important parameter being that the average particle size of the granules, must permit the formation of a directly compressible excipient which forms pharmaceutically acceptable tablets. The desired tap and bulk densities of the granulation of the present invention are normally between from about 0.3 to about 0.8 g/ml, with an average density of from about 0.5 to about 0.7 g/ml. For best results, the tablets formed from the granulations of the present invention are from about 6 to about 8 kg hardness. The average flow of the granulations prepared in accordance with the present invention are from about 25 to about 40 g/sec. Tablets compacted using an instrumented rotary tablet machine have been found to possess strength profiles which are largely independent of the inert saccharide component. Scanning electron photomicrographs of largely tablet surfaces have provided qualitative evidence of extensive plastic deformation on compaction, both at the tablet surface and across the fracture surface, and also show evidence of surface pores through which initial solvent ingress and solution egress may occur.

A wide variety of therapeutically active agents can be used in conjunction with the present invention. The therapeutically active agents (e.g. pharmaceutical agents) which may be used in the compositions of the present invention include both water soluble and water insoluble drugs. Examples of such therapeutically active agents include antihistamines (e.g., dimenhydrinate, diphenhydramine, chlorpheniramine and dexchlorpheniramine maleate), analgesics (e.g., aspirin, codeine, morphine, dihydromorphone, oxycodone, etc.), anti-inflammatory agents (e.g., naproxyn, diclofenac, indomethacin, ibuprofen, acetaminophen, aspirin, sulindac), gastro-intestinals and anti-emetics (e.g., metoclopramide), anti-epileptics (e.g., phenytoin, meprobamate and nitrezepam), vasodilators (e.g., nifedipine, papaverine, diltiazem and nicardirine), anti-tussive agents and expectorants (e.g., codeine phosphate), anti-asthmatics (e.g. theophylline), anti-spasmodics (e.g. atropine, scopolamine), hormones (e.g., insulin, heparin), diuretics (e.g., eltacrymic acid, bendrofluazide), anti-hypotensives (e.g., propranolol, clonidine), bronchodilators (e.g., albuterol), anti-inflammatory steroids (e.g., hydrocortisone, triamcinolone, prednisone), antibiotics (e.g., tetracycline), antihemorrhoidals, hypnotics, psychotropics, antidiarrheals, mucolytics, sedatives, decongestants, laxatives, antacids, vitamins, stimulants (including appetite suppressants such as phenylpropanolamine). The above list is not meant to be exclusive.

The ratio of medicament to the heterodisperse polysaccharide is based in part upon the relatively solubility of the medicament and the desired rate of release.

A computer aided pharmacokinetic model can be used to predict likely in vivo drug blood levels from condition-independent in-vitro drug profiles.

DETAILED DESCRIPTION OF THE PREFERRED EMBODIMENTS

The following examples illustrate various aspects of the present invention. They are not to be construed to limit the claims in any manner whatsoever.

EXAMPLE 1 (Prior Art)

Tablets containing appropriate amounts of propranolol hydrochloride together with a homodisperse polysaccharide (locust bean gum) and a heterodisperse polysaccharide controlled release excipient (xanthan gum/locust bean gum in a 1:1 ratio), inert pharmaceutical diluent (saccharide component), and 1% magnesium stearate are prepared either using direct compression or following wet granulation in a high speed mixer processor (Baker Perkins Ltd., Stoke on Trent, U.K.), as described in U.S. Pat. Nos. 4,994,276, 5,128,143 and 5,135,757. Tablets are compacted to approximately 14 kP crushing force and in vitro testing is carried out using an automated dissolution apparatus and the U.S.P. paddle method with a stirring speed of 50 rev min$^{-1}$. All of the dissolution studies are carried out in distilled water.

In vitro release profiles for propranolol hydrochloride tablets are found to have first order profiles using a homodisperse polysaccharide whereas a heterodisperse polysaccharide excipient provides a zero order release profile. It is believed that this resulted from a synergistic interaction between the homo- and heteropolysaccharides which occurs through cross linking of the polymer chains and alters some of the physical characteristics of the excipient, such as rate of glass-gel transition, polymer solubility, gel viscosity, rate of gelation and gel strength. Variation of the heterodisperse polysaccharide/saccharide component can also be used to modify drug release profiles further. Similar results are obtained when tablets are made using chlorpheniramine maleate and verapamil hydrochloride as the therapeutically active agents.

EXAMPLE 2—Prior Art

A slow release excipient is prepared by combining xanthan gum, locust bean gum, and dextrose in the amounts set forth in Table 1 below, and dry blending (Baker Perkin [Machine #5407], blender settings (chopper=1000 rpm, impeller=800 rpm)) the mixture for 2 minutes.

TABLE 1

| Excipient Granulation | | |
|---|---|---|
| Ingredient | % | g/1000 g |
| Xanthan gum | 25.0 | 225.0 |
| Locust bean gum | 25.0 | 225.0 |
| Dextrose | 50.0 | 450.0 |
| Total | 100.0% | 900 g |

Thereafter, water (115 ml) is added slowly and the mixture is blended for 1.5 minutes. The mixture is then dried overnight at 50° C. in an oven. Next, the mixture is screened through a 20 mesh screen, with particles larger than 20 mesh being discarded.

In Example 2, 354.5 grams of the granulated slow release excipient and 35.5 grams of phenylpropanolamine HCl are added into a 2 quart V-blender and blended for 10 minutes. Next, 8 grams of lubritab™ is added, and the mixture is blended for 5 minutes. Thereafter, 2.0 grams of magnesium stearate is added and the mixture is blended for 5 minutes. Finally, the mixture is tableted to provide tablets of approximately 846 mg and approximately 5–7 Kp. Further information concerning Example 2 is set forth in Table 2 below:

TABLE 2

| | Example 2 | | |
|---|---|---|---|
| Ingredient | mg/tablet | % | g/400 g |
| Excipient | 750.0 | 88.6 | 354.5 |
| Phenylpropanolamine | 75.0 | 8.9 | 35.5 |
| Lubritab | 17.0 | 2.0 | 8.0 |
| Magnesium stearate | 4.0 | 0.5 | 2.0 |
| Total | 846 mg/tab | 100% | 400 g |

EXAMPLES 3–10

In Example 3, the slow release granulation is prepared in similar fashion to Example 2, except that after the gums and dextrose are combined, 130 ml of water is added, and the mixture is dried in an aeromatic fluid bed dryer for 45 minutes at 70° C. (Type Strea-1). The ingredients of the slow release granulation of Example 3 are set forth in Table 3 below:

TABLE 3

| Excipient Granulation | | |
|---|---|---|
| Ingredient | % | g/1000 g |
| Xanthan gum | 25.0 | 250.0 |
| Locust bean gum | 25.0 | 250.0 |

TABLE 3-continued

| | Excipient Granulation | |
|---|---|---|
| Ingredient | % | g/1000 g |
| Dextrose | 50.0 | 500.0 |
| Total | 100.0% | 1000 g |

Thereafter, 336.4 grams of the granulated slow release excipient and 33.6 grams of phenylpropanolamine HCl are added into a 2 quart V-blender and blended for 10 minutes. Next, 20.0 grams of surfactant (sodium lauryl sulfate) and 8 grams of lubritab™ are added, and the mixture is blended for 5 minutes. Thereafter, 2.0 grams of magnesium stearate is added and the mixture is blended for 5 minutes. Finally, the mixture is tableted to provide tablets of approximately 892 mg and approximately 5-7 Kp. Further information concerning Example 3 is set forth in Table 4 below:

TABLE 4

| | Example 3 | | |
|---|---|---|---|
| Ingredient | mg/tablet | % | g/400 g |
| Excipient | 750/0 | 84.1 | 336.4 |
| Phenylpropanolamine | 75.0 | 8.4 | 33.6 |
| *Surfactant (SLS) | 44.7 | 5.0 | 20.0 |
| Lubritab | 17.8 | 2.0 | 8.0 |
| Magnesium stearate | 4.5 | 0.5 | 2.0 |
| Total | 892 mg/tab | 100.0% | 400 g |

Examples 4–10 are prepared in similar fashion to Example 3. In each of Examples 4–10, the formulations are dry blended with a 1:5 drug:gum ratio. The percent of gum in the xanthan gum/locust bean gum/dextrose mixture in each formulation is 50%. Each formulation contains 75 mg phenylpropanolamine HCl and 750 mg of the slow release excipient granulation, and this mixture is blended in a 2 quart v-blender for 10 minutes. Then, 2% lubritab is added along with the surfactant, and blended for 5 minutes. The surfactant used is sodium lauryl sulfate and/or docusate sodium. Finally, 0.5% of magnesium stearate is added and the mixture is blended for 5 minutes, and tableted to the specified tablet weight. The tablet weights, amount (percentage) and type of surfactants used in Examples 3–10 are set forth in Table 5 below:

TABLE 5

| Example | Surfactant* | Granulation % Surfactant | Tablet wt. (mg) |
|---|---|---|---|
| Ex. 3 | SLS | 2 | 863.9 |
| Ex. 4 | SLS | 5 | 891.9 |
| Ex. 5 | SLS | 10 | 942.9 |
| Ex. 6 | DSS | 2 | 863.9 |
| Ex. 7 | DSS | 5 | 891.9 |
| Ex. 8 | DSS | 10 | 942.9 |
| Ex. 9 | SLS + DSS | 1 + 1 | 863.9 |
| Ex. 10 | SLS + DSS | 2 + 2 | 882.4 |

*SLS refers to sodium lauryl sulfate, and DSS refers to docusate sodium.

EXAMPLES 11–12

DISSOLUTION TESTS—PERCENT DISSOLVED OVER TIME AND RELEASE RATE

Next, dissolution studies are conducted for the tablets of Examples 2–10 in order to determine the percent dissolved of drug over time, as well as the release rate of the drug (phenylpropanolamine HCl). The dissolution tests were conducted in a DI water medium having a volume of 1000 mL by the paddle method. The mixer rotation is 100 rpm, the height is 2.5 cm, the temperature is 37° C., and the wavelength used is 210 nm. The calibration factor is determined according to the following equation:

$$\text{calibration factor} = \frac{\text{concentration of standard} * 100}{\text{concentration of sample} * \text{absorbance of std}}$$

The percent of the drug dissolved is then determined according to the following equation:

$$\% \text{ active dissolved} = \text{calibration factor} * \text{absorbance of sample}$$

The dissolution and release rate data for Examples 2–10 is based on a 6 tablet dissolution study. The dissolution results expressed as percent dissolved are set forth in Tables 6–8 below:

TABLE 6

| | Examples 2–5 | | | |
|---|---|---|---|---|
| | Percent Dissolved *(phenylpropanolamine HCl)* | | | |
| Time (hours) | Ex. 2 no SLS | Ex. 3 2% SLS | Ex. 4 5% SLS | Ex. 5 10% SLS |
| 1 | 22.0% | 20.8% | 15.3% | 7.0% |
| 2 | 34.4 | 33.2 | 23.6 | 11.7 |
| 3 | 42.5 | 41.6 | 29.6 | 15.4 |
| 4 | 49.6 | 48.5 | 34.9 | 19.2 |
| 5 | 56.0 | 54.6 | 40.4 | 24.8 |
| 6 | 62.9 | 62.8 | 48.2 | 31.6 |
| 7 | 69.5 | 73.0 | 69.6 | 39.6 |
| 8 | 74.6 | 87.9 | 77.9 | 52.2 |
| 9 | 78.1 | 91.2 | 82.2 | 55.1 |
| 10 | 80.7 | 95.9 | 85.2 | 56.7 |
| 11 | 83.6 | 96.0 | 88.6 | 58.8 |
| 12 | 87.8 | 98.0 | 91.1 | 60.1 |
| 13 | 90.6 | 98.0 | 94.1 | 61.6 |
| 14 | 94.2 | 99.6 | 96.8 | 67.0 |
| 15 | 98.7 | 100.0 | 98.9 | 73.5 |
| 16 | 100.0 | — | 100.0 | 79.7 |
| 17 | — | — | — | 83.1 |
| 18 | — | — | — | 90.0 |
| 19 | — | — | — | 96.0 |
| 20 | — | — | — | 100.0 |

TABLE 7

| | Examples 2 and 6–8 | | | |
|---|---|---|---|---|
| | Percent Dissolved *(phenylpropanolamine HCl)* | | | |
| Time (hours) | Ex. 2 no DSS | Ex. 6 2% DSS | Ex. 7 5% DSS | Ex. 8 10% DSS |
| 1 | 22.0 | 17.7 | 15.4 | 15.2 |
| 2 | 34.4 | 27.1 | 23.3 | 22.8 |
| 3 | 42.5 | 33.9 | 29.1 | 28.4 |
| 4 | 49.6 | 39.4 | 34.0 | 33.4 |
| 5 | 56.0 | 44.6 | 38.9 | 40.7 |
| 6 | 62.9 | 52.0 | 46.2 | 55.4 |
| 7 | 69.5 | 64.8 | 59.2 | 65.4 |
| 8 | 74.6 | 66.0 | 66.3 | 67.6 |

TABLE 7-continued

Examples 2 and 6–8
Percent Dissolved *(phenylpropanolamine HC1)*

| Time (hours) | Ex. 2 no DSS | Ex. 6 2% DSS | Ex. 7 5% DSS | Ex. 8 10% DSS |
|---|---|---|---|---|
| 9 | 78.1 | 70.9 | 69.7 | 69.3 |
| 10 | 80.7 | 75.2 | 71.6 | 70.3 |
| 11 | 83.6 | 78.5 | 75.2 | 75.7 |
| 12 | 87.8 | 87.0 | 77.1 | 78.6 |
| 13 | 90.6 | 94.3 | 79.8 | 79.3 |
| 14 | 94.2 | 94.3 | 84.0 | 82.2 |
| 15 | 98.7 | 98.5 | 88.1 | 86.9 |
| 16 | 100.0 | 100.0 | 93.5 | 89.5 |
| 17 | — | — | 92.8 | 90.9 |
| 18 | — | — | 95.4 | 93.2 |
| 19 | — | — | 97.4 | 94.2 |
| 20 | — | — | 99.4 | 96.1 |
| 21 | — | — | 100.0 | 97.2 |
| 22 | — | — | — | 98.5 |
| 23 | — | — | — | 99.3 |
| 24 | — | — | — | 100.0 |

TABLE 8

Examples 2 and 9–10
Percent Dissolved *(phenylpropanolamine HC1)*

| Time (hours) | Ex. 2 no SLS + DSS | Ex. 9 1% SLS + 1% DSS | Ex. 10 2% SLS + 2% DSS |
|---|---|---|---|
| 1 | 22.0 | 15.5 | 16.5 |
| 2 | 34.4 | 22.6 | 26.5 |
| 3 | 42.5 | 28.2 | 33.5 |
| 4 | 49.6 | 32.8 | 38.0 |
| 5 | 56.0 | 36.9 | 46.4 |
| 6 | 62.9 | 40.7 | 54.8 |
| 7 | 69.5 | 45.0 | 61.5 |
| 8 | 74.6 | 51.4 | 67.7 |
| 9 | 78.1 | 56.9 | 68.6 |
| 10 | 80.7 | 61.0 | 73.5 |
| 11 | 83.6 | 64.2 | 78.9 |
| 12 | 87.8 | 68.7 | 83.2 |
| 13 | 90.6 | 73.8 | 85.2 |
| 14 | 94.2 | 77.3 | 87.0 |
| 15 | 98.7 | 78.4 | 90.2 |
| 16 | 100.0 | 85.4 | 94.0 |
| 17 | — | 88.3 | 97.5 |
| 18 | — | 93.0 | 99.3 |
| 19 | — | 96.1 | 100.0 |
| 20 | — | 98.5 | — |
| 21 | — | 99.1 | — |
| 22 | — | 100.0 | — |

Figure 4:
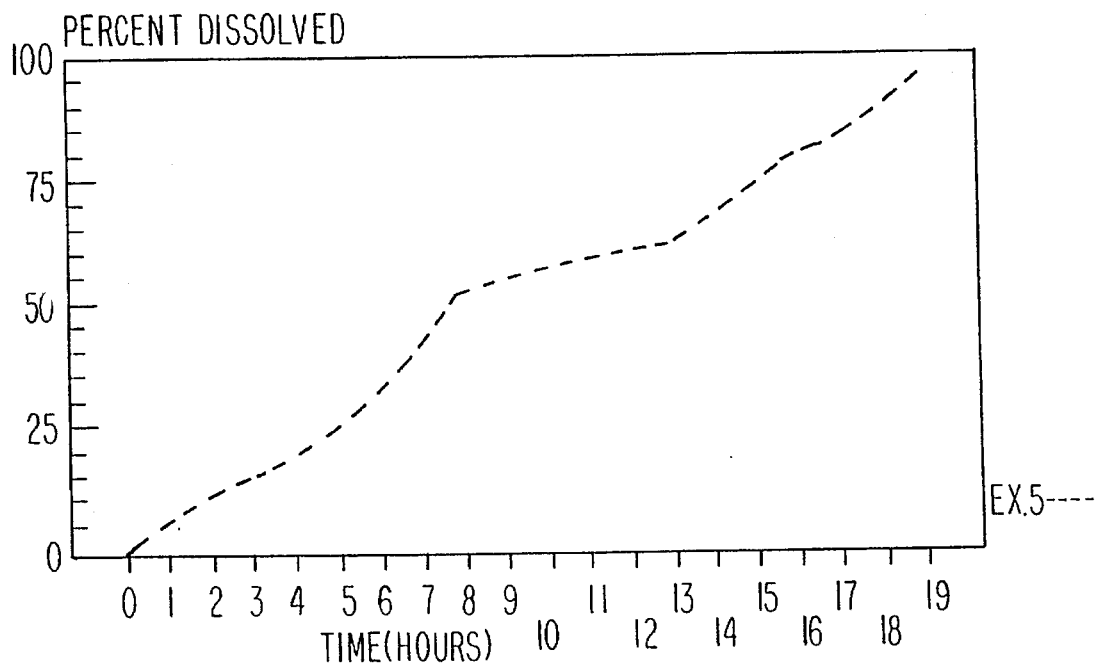
Figure 5:
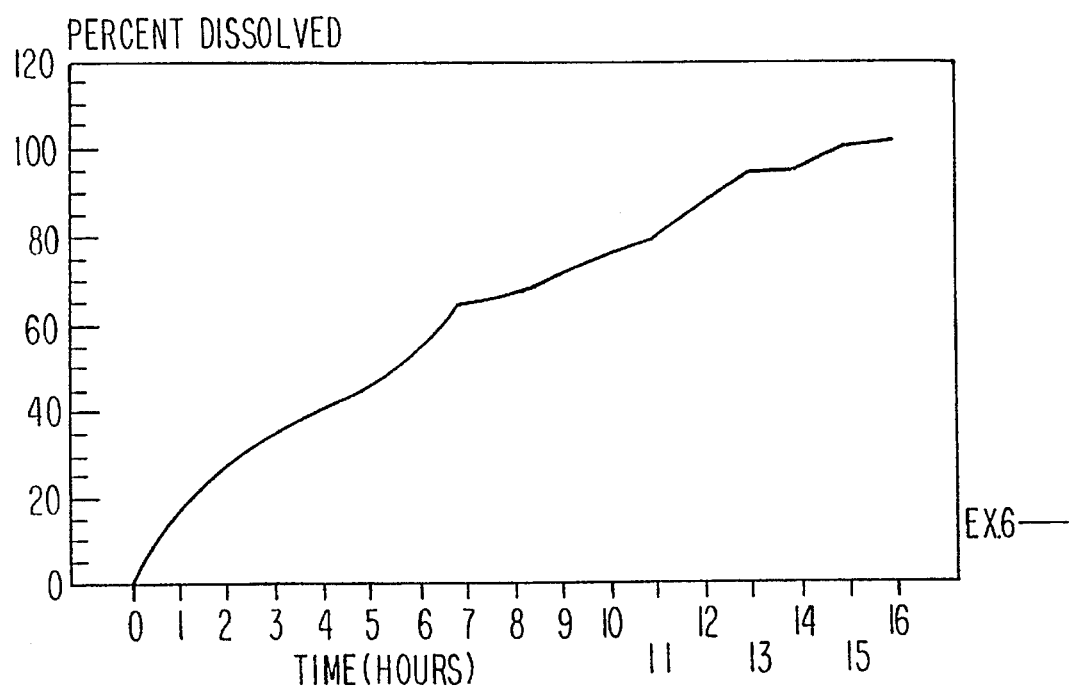
Figure 6:
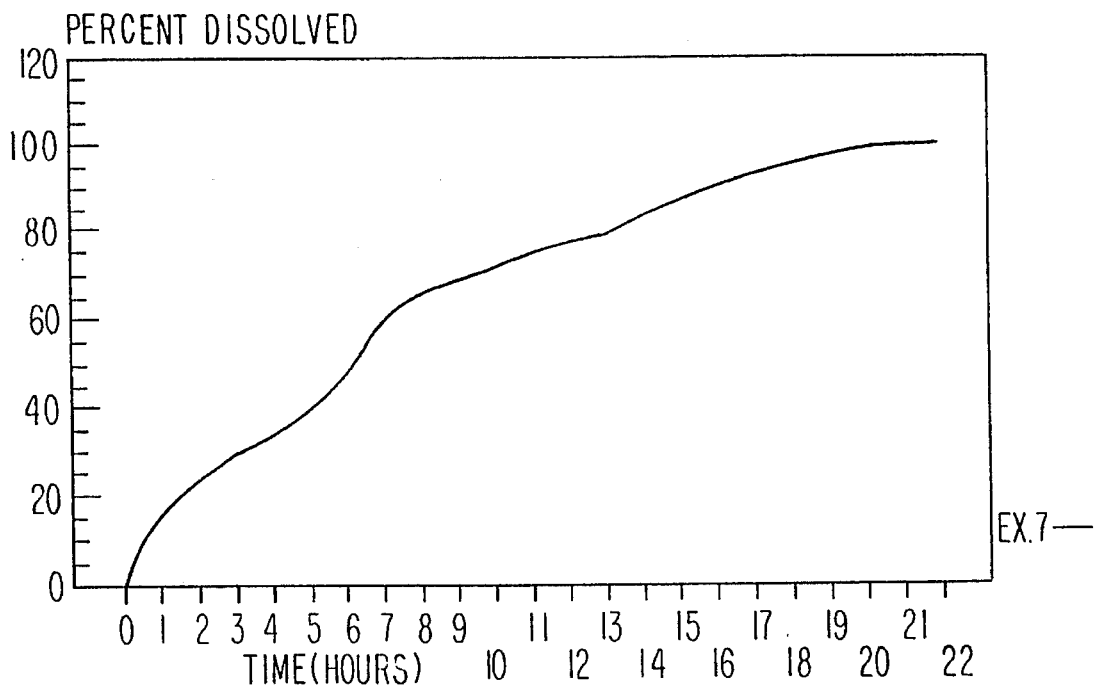
Figure 7:
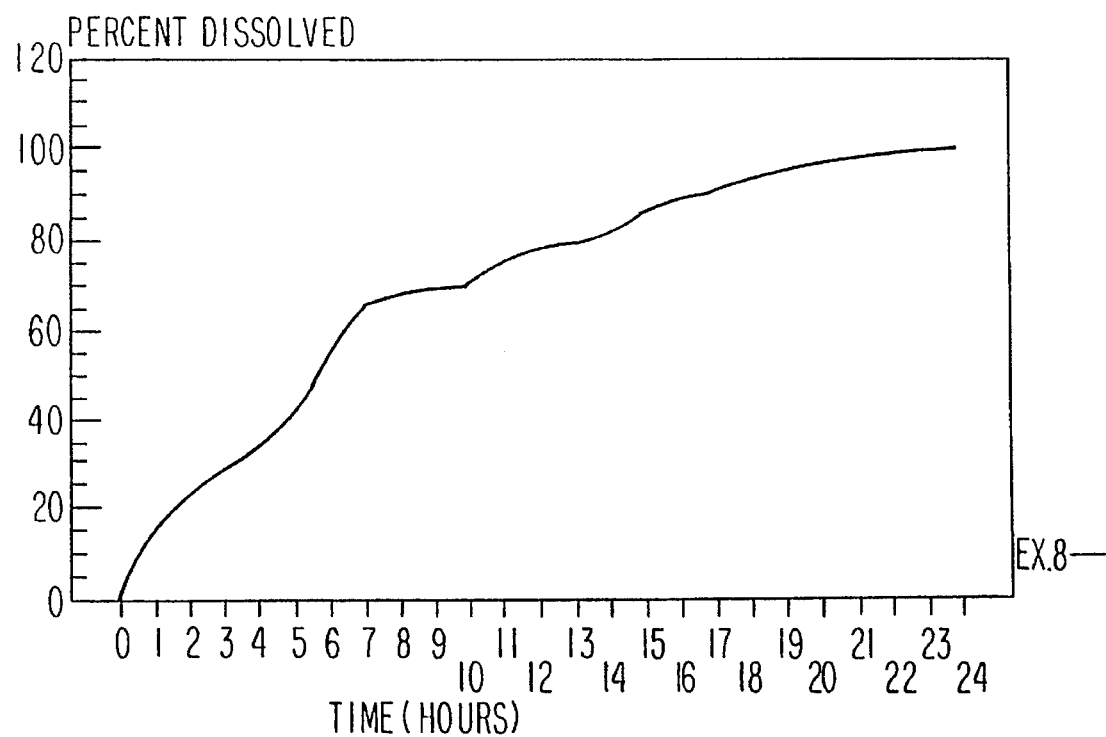
Figure 8:
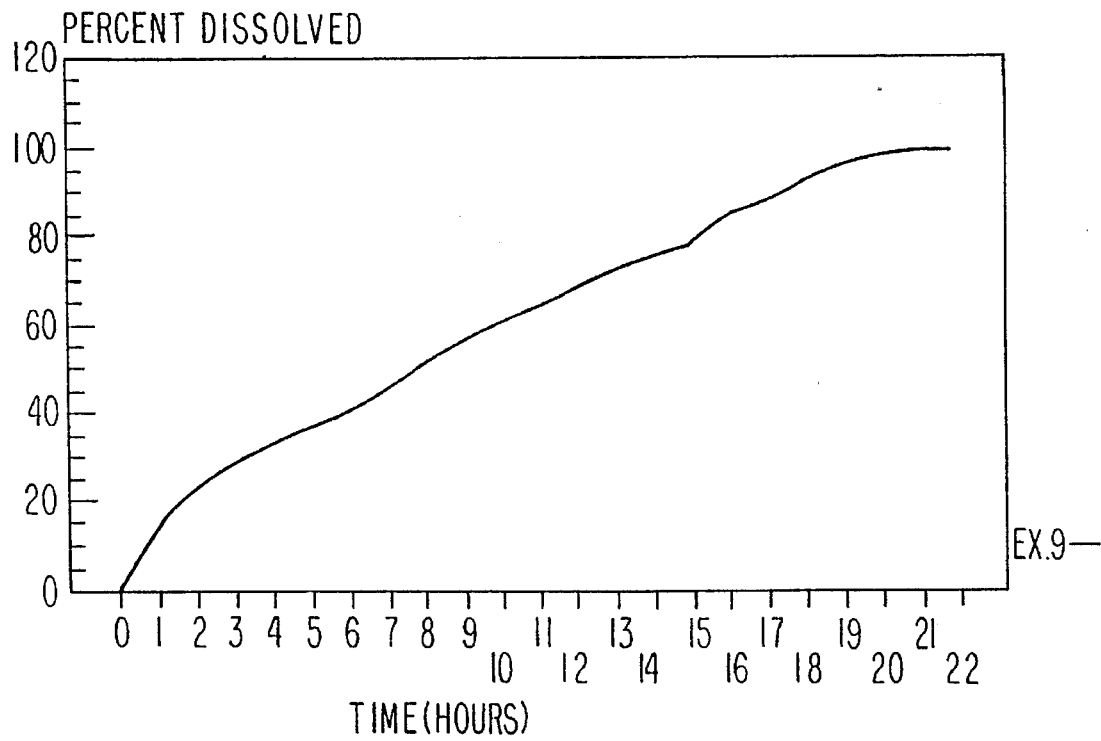
Figure 9:
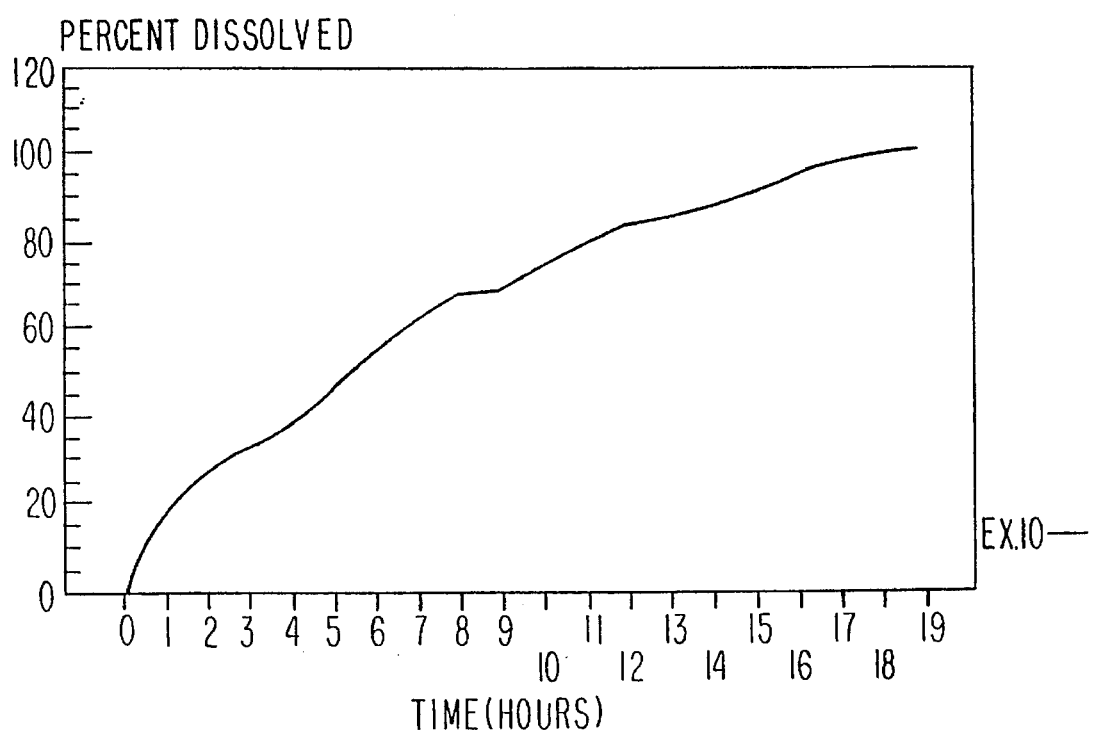

FIGS. 1–9 are graphical representations of the dissolution curves (expressed as percent dissolved over time) provided by the tablets of Example 2 (no surfactant added) and Examples 3–10 (surfactant(s) included), respectively.

The dissolution results for Examples 2–10 are expressed as release rates are set forth in Tables 9–11 below:

TABLE 9

Examples 2–5
Release Rate *(phenylpropanolamine HC1)*

| Time (hours) | Ex. 2 no SLS | Ex. 3 2% SLS | Ex. 4 5% SLS | Ex. 5 10% SLS |
|---|---|---|---|---|
| 1 | 22.0 | 20.8 | 15.3 | 7.0 |
| 2 | 12.4 | 12.4 | 8.30 | 4.70 |
| 3 | 8.10 | 8.40 | 6.00 | 3.7 |
| 4 | 7.10 | 6.90 | 5.30 | 3.80 |
| 5 | 6.40 | 6.10 | 5.50 | 5.60 |

TABLE 9-continued

Examples 2–5
Release Rate *(phenylpropanolamine HC1)*

| Time (hours) | Ex. 2 no SLS | Ex. 3 2% SLS | Ex. 4 5% SLS | Ex. 5 10% SLS |
|---|---|---|---|---|
| 6 | 6.90 | 8.20 | 7.80 | 6.80 |
| 7 | 6.60 | 10.2 | 21.4 | 8.00 |
| 8 | 5.10 | 14.9 | 8.30 | 12.6 |
| 9 | 3.50 | 3.30 | 4.30 | 2.90 |
| 10 | 2.60 | 4.70 | 3.00 | 1.60 |
| 11 | 2.90 | 0.10 | 3.40 | 2.10 |
| 12 | 4.20 | 2.00 | 2.50 | 1.30 |
| 13 | 2.80 | 0.00 | 3.00 | 1.50 |
| 14 | 3.60 | 1.60 | 2.70 | 5.40 |
| 15 | 4.70 | 0.40 | 2.10 | 6.50 |
| 16 | 1.30 | 0.00 | 1.10 | 6.20 |
| 17 | 0.00 | — | 0.00 | 3.40 |
| 18 | — | — | — | 6.90 |
| 19 | — | — | — | 6.00 |
| 20 | — | — | — | 4.00 |
| 21 | — | — | — | 0.00 |

TABLE 10

Examples 2 and 6–8
Release Rate *(phenylpropanolamine HC1)*

| Time (hours) | Ex. 2 no DSS | Ex. 6 2% DSS | Ex. 9 5% DSS | Ex. 10 10% DSS |
|---|---|---|---|---|
| 1 | 22.0 | 17.7 | 15.4 | 15.2 |
| 2 | 12.4 | 9.40 | 7.90 | 7.60 |
| 3 | 8.10 | 6.80 | 5.80 | 5.60 |
| 4 | 7.10 | 5.50 | 4.90 | 5.00 |
| 5 | 6.40 | 5.2 | 4.90 | 7.30 |
| 6 | 6.90 | 7.40 | 7.30 | 14.7 |
| 7 | 6.60 | 12.8 | 13.0 | 10.0 |
| 8 | 5.10 | 1.20 | 7.10 | 2.20 |
| 9 | 3.50 | 4.90 | 3.40 | 1.70 |
| 10 | 2.60 | 4.30 | 1.90 | 1.00 |
| 11 | 2.90 | 3.30 | 2.70 | 5.40 |
| 12 | 4.20 | 8.50 | 4.20 | 2.90 |
| 13 | 2.80 | 7.30 | 4.10 | 0.70 |
| 14 | 3.60 | 0.00 | 2.40 | 2.90 |
| 15 | 4.70 | 4.20 | 2.30 | 4.70 |
| 16 | 1.30 | 1.50 | 2.60 | 2.60 |
| 17 | 0.00 | 0.00 | 2.00 | 1.40 |
| 18 | — | — | 2.00 | 2.30 |
| 19 | — | — | 0.60 | 1.00 |
| 20 | — | — | 0.00 | 1.90 |
| 21 | — | — | — | 1.10 |
| 22 | — | — | — | 0.80 |
| 23 | — | — | — | 0.70 |
| 24 | — | — | — | 0.00 |

TABLE 11

Examples 2 and 9–10
Release Rate *(phenylpropanolamine HC1)*

| Time (hours) | Ex. 2 no SLS + DSS | Ex. 9 1% SLS + 1% DSS | Ex. 10 2% SLS + 2% DSS |
|---|---|---|---|
| 1 | 22.0 | 15.5 | 16.5 |
| 2 | 12.4 | 7.10 | 10.0 |
| 3 | 8.10 | 5.60 | 7.00 |
| 4 | 7.10 | 4.60 | 4.50 |
| 5 | 6.40 | 4.10 | 8.40 |
| 6 | 6.90 | 3.80 | 8.40 |
| 7 | 6.60 | 4.30 | 6.70 |
| 8 | 5.10 | 10.7 | 6.20 |
| 9 | 3.50 | 5.50 | 0.90 |
| 10 | 2.60 | 4.10 | 4.90 |
| 11 | 2.90 | 3.20 | 5.40 |

TABLE 11-continued

Examples 2 and 9–10
Release Rate *(phenylpropanolamine HCl)*

| Time (hours) | Ex. 2 no SLS + DSS | Ex. 9 1% SLS + 1% DSS | Ex. 10 2% SLS + 2% DSS |
|---|---|---|---|
| 12 | 4.20 | 4.50 | 4.30 |
| 13 | 2.80 | 5.10 | 2.00 |
| 14 | 3.60 | 3.50 | 1.80 |
| 15 | 4.70 | 1.10 | 3.20 |
| 16 | 1.30 | 7.00 | 3.80 |
| 17 | 0.00 | 2.90 | 3.50 |
| 18 | — | 4.70 | 1.80 |
| 19 | — | 3.10 | 0.70 |
| 20 | — | 2.40 | 0.00 |
| 21 | — | 0.60 | — |
| 22 | — | 0.90 | — |
| 23 | — | 0.00 | — |

Figure 10:
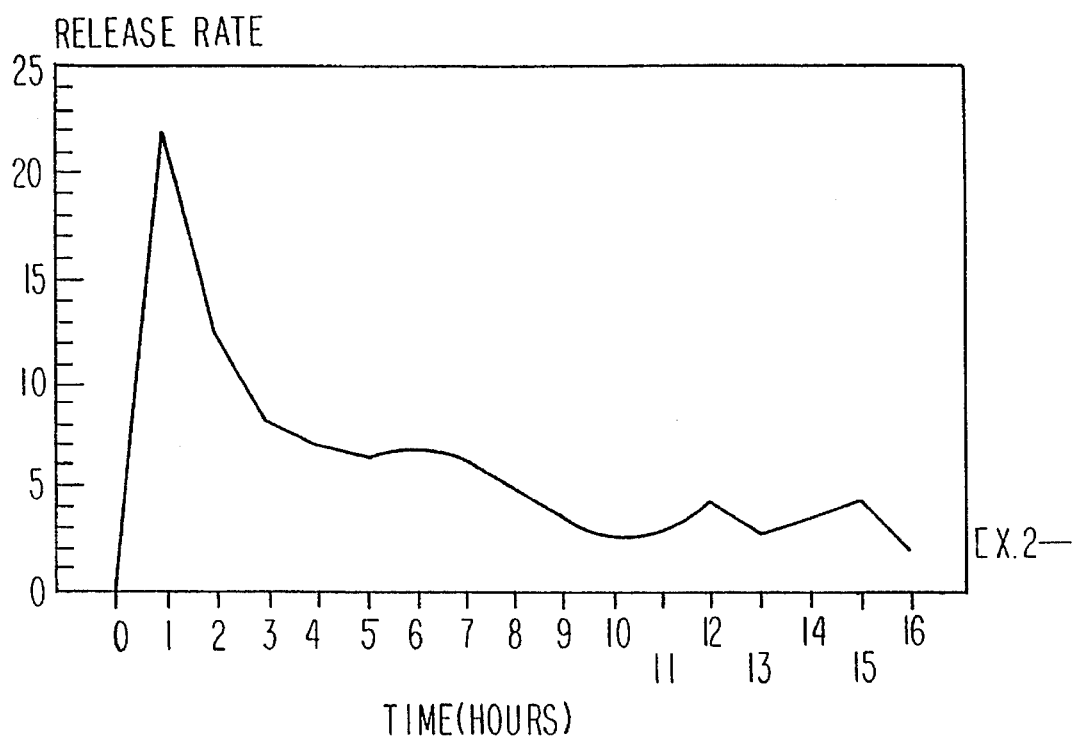
FIG. 10 is a graphical representation of the dissolution curve (expressed as release rate over time) provided by the tablets of Example 2 (no surfactant)
Figure 11:
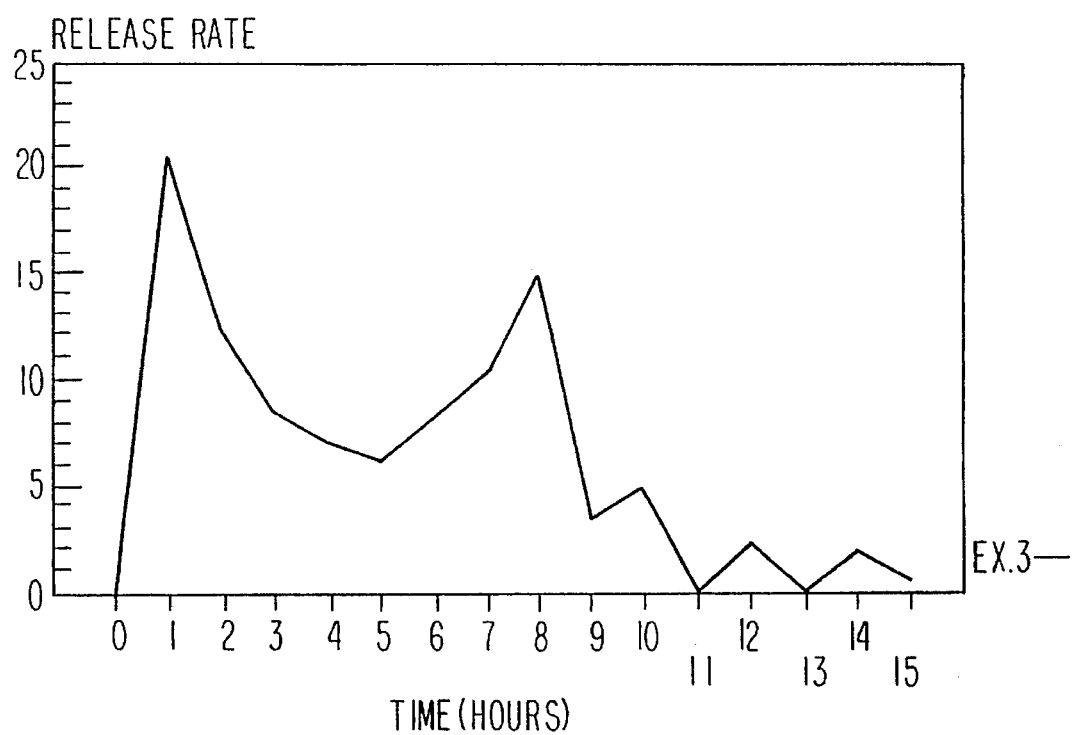
Figure 12:
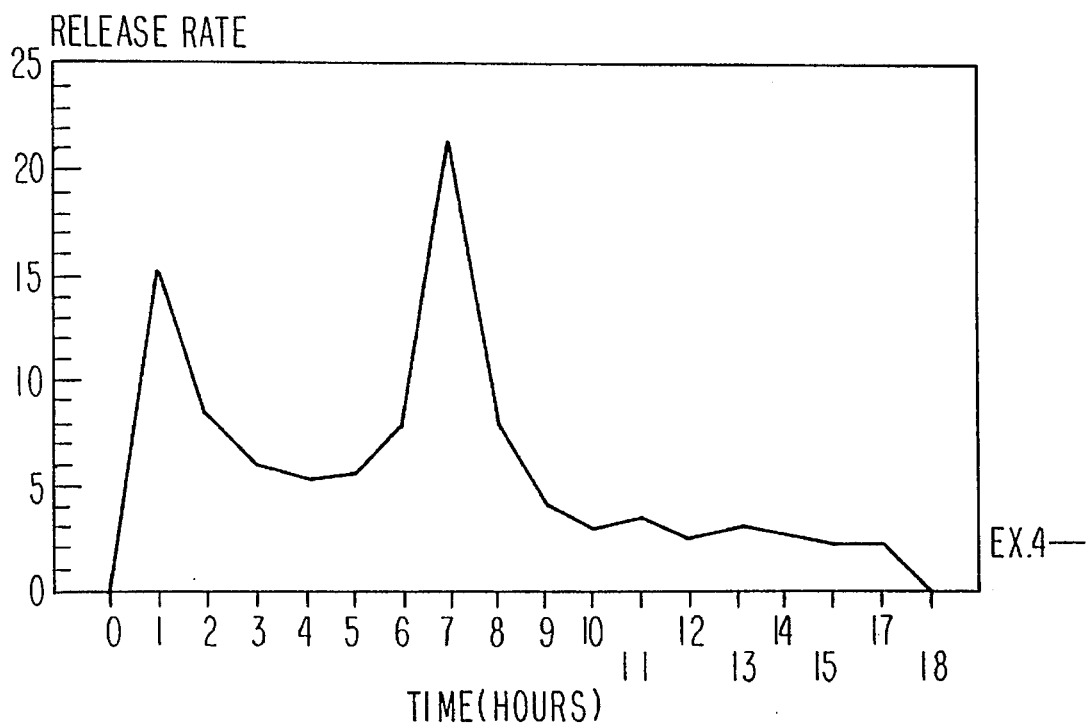
Figure 13:
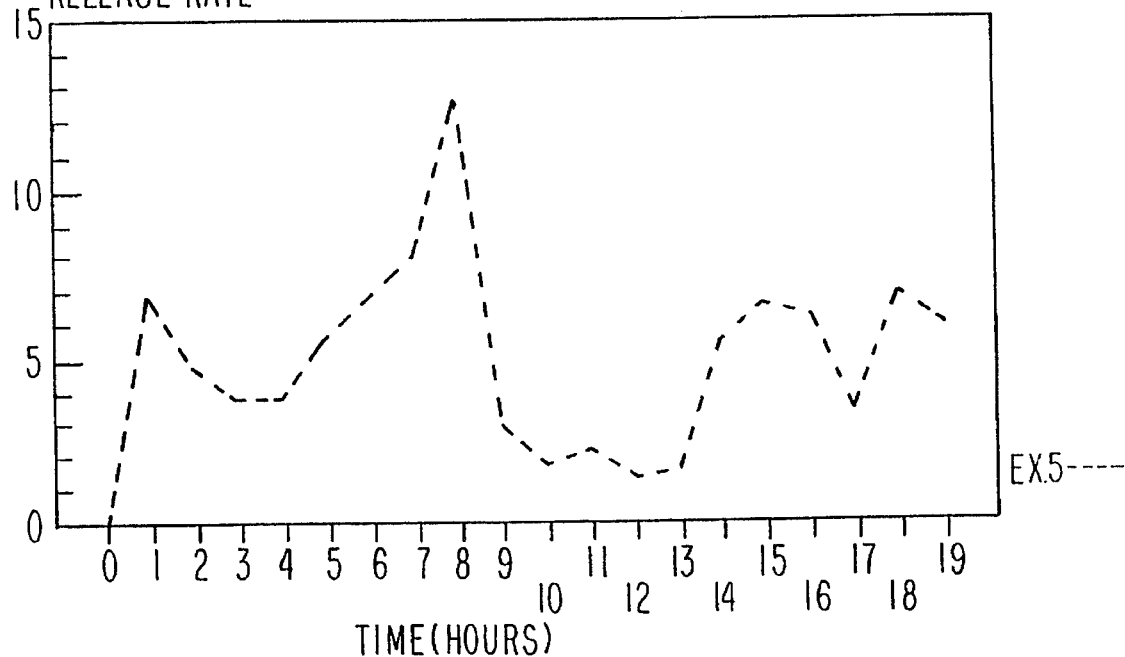
Figure 14:
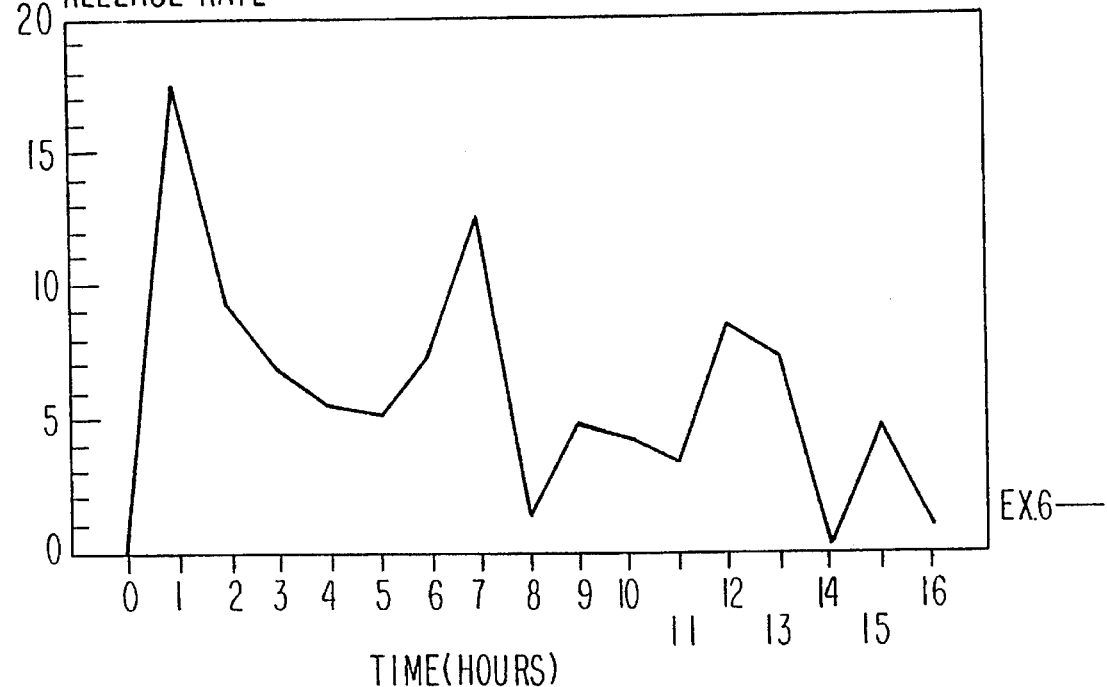
Figure 17:
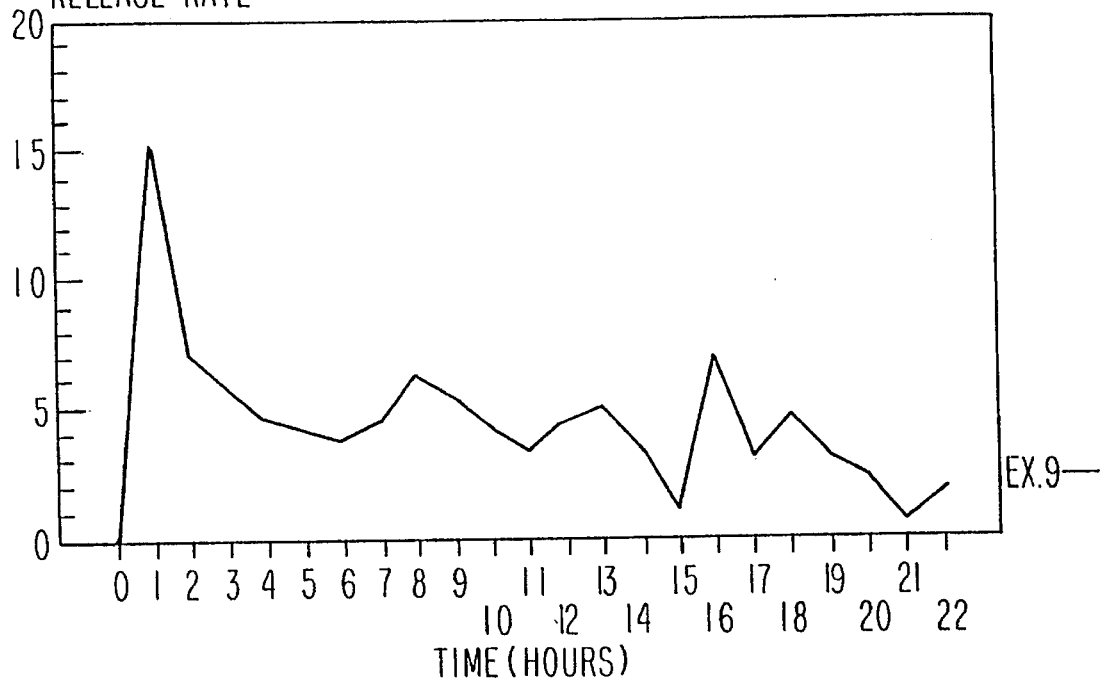
Figure 18:
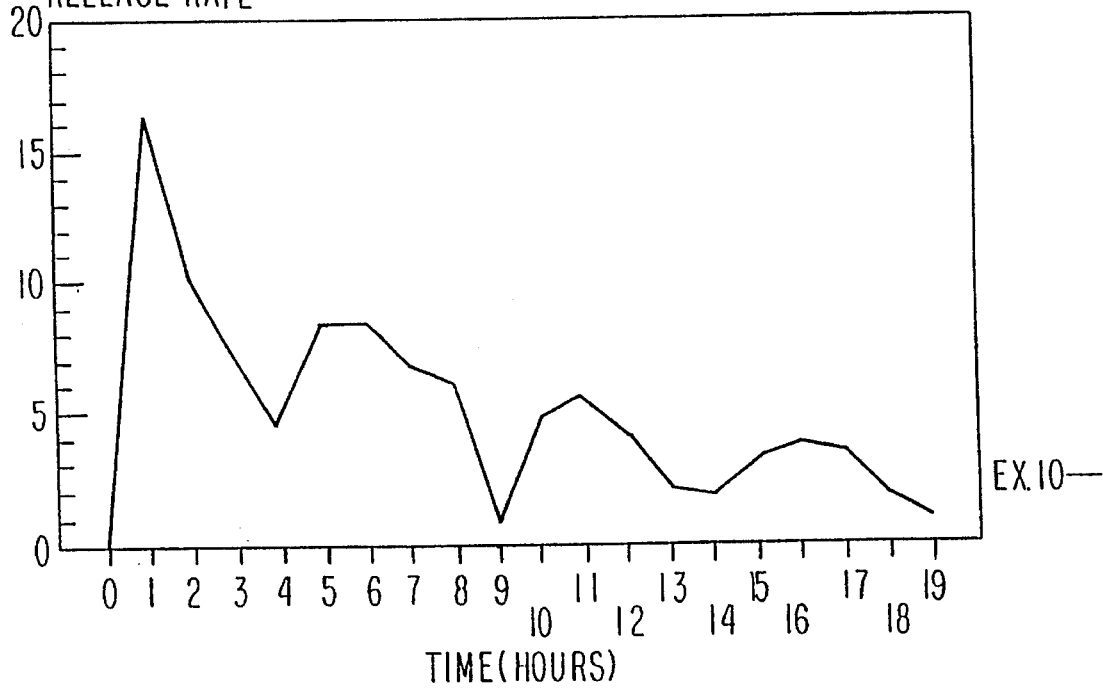

FIGS. 10–18 are graphical representations of the dissolution curves (expressed as release rate over time) provided by the tablets of Example 2 (no surfactant added) and Examples 3–10 (surfactant(s) included). As is readily apparent from the results, the formulations of Examples 3–10 provide a multi-phasic release of phenylpropanolamine HCl.

EXAMPLES 13–16

Preparation of Controlled Release Excipient For Multiphasic Dosage Forms

Controlled release excipients for multiphasic dosage forms according to the present application are prepared as follows, In Examples 13–14, 250 grams of xanthan gum, 250 grams of locust bean gum, 50 grams of surfactant and 450 grams of dextrose are blended for two minutes in a mixer (Baker Perkins blender), blender setting (chopper=1,000 rpm, impeller=800 rpm).

In Examples 15–16, 100 grams of surfactant and 400 grams of dextrose are blended with 250 grams of xanthan gum and 250 grams of locust bean gum for two minutes.

The surfactant in Examples 13 and 16 is sodium lauryl sulfate (SLS), while in Examples 14 and 15, the surfactant is docusate sodium succinate (DSS).

Thereafter, about 112 ml of water is slowly added to the mixtures and then blended for an additional 1.5 minutes. The mixed product, which is now in the form of granules, is removed from the blender and dried in an aeromatic fluid bed dryer (type: Strea-1) for 30 minutes at a temperature of 70° C. The dried granulation is then passed through a 20 mesh screen.

In Examples 13–14, the final composition of the mixture is 25.0% xanthan gum, 25.0% locust bean gum, 5.0% surfactant and 45.0% dextrose by weight. In Examples 15–16, the final composition of the mixture is 25.0% xanthan gum, 25.0% locust bean gum, 10.0% surfactant and 40.0% dextrose by weight.

The product of Examples 13–16 is now ready to be used as a controlled release excipient for multiphasic dosage forms, and may now be admixed with one or more active ingredients and any other pharmaceutically necessary additives, and tableted.

The weight and percentages of the ingredients for the controlled release excipients used in Examples 13–16 are set forth in Tables 12–15 below:

TABLE 12
EXAMPLE 13

| Ingredient | g/1000 g | % |
|---|---|---|
| Xanthan Gum | 250.0 | 25.0 |
| Locust Bean Gum | 250.0 | 25.0 |
| Surfactant (TYPE) | 50.0 (SLS) | 5.0 |
| Dextrose | 450.0 | 45.0 |
| TOTAL | 1000 g | 100% |

TABLE 13
EXAMPLE 14

| Ingredient | g/1000 g | % |
|---|---|---|
| Xanthan Gum | 250.0 | 25.0 |
| Locust Bean Gum | 250.0 | 25.0 |
| Surfactant (TYPE) | 50.0 (DSS) | 5.0 |
| Dextrose | 450.0 | 45.0 |
| TOTAL | 1000 g | 100% |

TABLE 14
EXAMPLE 15

| Ingredient | g/1000 g | % |
|---|---|---|
| Xanthan Gum | 250.0 | 25.0 |
| Locust Bean Gum | 250.0 | 25.0 |
| Surfactant (TYPE) | 100.0 (DSS) | 10.0 |
| Dextrose | 400.0 | 40.0 |
| TOTAL | 1000 g | 100% |

TABLE 15
EXAMPLE 20

| Ingredient | g/1000 g | % |
|---|---|---|
| Xanthan Gum | 250.0 | 25.0 |
| Locust Bean Gum | 250.0 | 25.0 |
| Surfactant (TYPE) | 100.0 (SLS) | 10.0 |
| Dextrose | 400.0 | 40.0 |
| TOTAL | 1000 g | 100% |

EXAMPLES 17–21

Preparation of Controlled Release Tablets

Controlled release tablets according to the present invention are prepared as follows.

In Examples 17–19, 278.43 grams of the excipient of the present invention is first blended with 27.82 grams of phenylpropanolamine HCl for 10 minutes in a 2-quart V-blender.

The excipient of Example 13 is used in Example 17, the excipient of Example 14 is used in Example 18 and the excipient of Example 16 is used in Example 19.

After the initial blending of the mixtures in Examples 17–19, 7 grams of Lubritab™ and 35 grams of MCC-50M are blended with each mixture for an additional 5 minutes. Thereafter, 1.75 grams of magnesium stearate is added to the mixtures of Examples 17–19, and then blended for another 5 minutes.

Finally, the mixtures in Examples 17–19 are tableted to provide tablets of approximately 942.8 mg and approximately 2.0 Kp.

In Examples 17–19, the final composition of the mixture is 79.5% excipient, 7.95% phenylpropanolamine HCl, 2.0% Lubritab™, 10.0% MCC-50M and 0.5% of magnesium stearate by weight. Further information concerning Examples 17–19 are set forth in Tables 16–18 below:

TABLE 16

| | EXAMPLE 17 | | |
|---|---|---|---|
| Ingredient | mg/tab | % | g/350 g |
| Excipient | 750.0 | 79.55 | 278.43 |
| PPA | 750.0 | 7.95 | 27.82 |
| Lubritab | 18.86 | 2.00 | 7.00 |
| MCC-50M | 94.28 | 10.00 | 35.00 |
| Mag. Stear. | 4.71 | 0.50 | 1.75 |
| TOTAL | 942.85 mg/tab | 100% | 350 g |

PPA HCl = Phenylpropanolainine Hydrogen Chloride
Mag. Stear. = Magnesium Stearate

TABLE 17

| | EXAMPLE 18 | | |
|---|---|---|---|
| Ingredient | mg/tab | % | g/350 g |
| Excipient | 750.0 | 79.55 | 278.43 |
| PPA | 75.0 | 7.95 | 27.82 |
| Lubritab | 18.86 | 2.00 | 7.00 |
| MCC-50M | 94.28 | 10.00 | 35.00 |
| Mag. Stear. | 4.71 | 0.50 | 1.75 |
| TOTAL | 942.85 mg/tab | 100% | 350 g |

PPA HCl = Phenylpropanolamine Hydrogen Chloride
Mag. Stear. = Magnesium Stearate

TABLE 18

| | EXAMPLE 19 | | |
|---|---|---|---|
| Ingredient | mg/tab | % | g/350 g |
| Excipient | 750.0 | 79.55 | 278.43 |
| PPA | 75.0 | 7.95 | 27.82 |
| Lubritab | 18.86 | 2.00 | 7.00 |
| MCC-50M | 94.28 | 10.00 | 35.00 |
| Mag. Stear. | 4.71 | 0.50 | 1.75 |
| TOTAL | 942.85 mg/tab | 100% | 350 g |

PPA HCl = Phenylpropanolamine Hydrogen Chloride
Mag. Stear. = Magnesium Stearate In Example 20, 292.50 grams of the excipient of Example 13 are blended with 48.75 grams of phenylpropanolamine HCl for 10 minutes in a 2-quart V-blender.

After the initial blending, 7 grams of Lubritab™ and 1.75 grams of magnesium stearate are added to the mixture which is then blended for another 5 minutes.

Finally, the mixture is tableted to provide tablets of approximately 538.46 mg and approximately 20 Kp.

In Example 20, the final composition of the mixture is 83.57% excipient of Example 13, 13.93% phenylpropanolamine HCl, 2.0% Lubritab™ and 0.5% magnesium stearate by weight. Further information concerning Example 20 is set forth in Table 19 below:

TABLE 19

| | EXAMPLE 20 | | |
|---|---|---|---|
| Ingredient | mg/tab | % | g/350 g |
| Excipient | 450.0 | 83.57 | 292.50 |
| PPA HCl | 75.0 | 13.93 | 48.75 |
| Lubritab | 10.77 | 2.00 | 7.00 |
| Mag Stear. | 2.69 | 0.50 | 1.75 |
| TOTAL | 538.46 mg/tab | 100% | 350 g |

PPA HCl = Phenylpropanolamine Hydrogen Chloride
Mag. Stear. = Magnesium Stearate In Example 21, 487.5 grams of the excipient of Example 15 is first blended with 48.75 grams of phenylpropanolamine HCl for 10 minutes in a 2-quart V-blender.

After the initial blending, 11 grams of Lubritab™ and 2.75 grams of magnesium stearate is added to the mixture and blended for an additional 5 minutes.

The mixture is then tableted to provide tablets of approximately 846.15 mg and approximately 2.0 kg.

In Example 21, the final composition of the mixture is 88.64% excipient of Example 15, 8.86% phenylpropanolamine HCl, 2.0% Lubritab™ and 0.5% magnesium stearate by weight. Further information concerning Example 21 is set forth in Table 20 below:

TABLE 20

| | EXAMPLE 21 | | |
|---|---|---|---|
| Ingredient | mg/tab | % | G/350 g |
| Excipient | 750.0 | 88.64 | 487.50 |
| PPA HCl | 75.0 | 8.86 | 48.75 |
| Lubritab ™ | 16.92 | 2.00 | 11.00 |
| Mag. Stear. | 4.23 | 0.50 | 2.75 |
| TOTAL | 846.15 mg/tab | 100% | 550 g |

PPA HCl = Phenylpropanolamine Hydrogen Chloride
Mag. Stear. = Magnesium Stearate The examples provided above are not meant to be exclusive. Many other variations of the present invention would be obvious to those skilled in the art, and are contemplated to be within the scope of the appended claims.

What is claimed is:

1. A controlled release multi-phasic pharmaceutical excipient, comprising:

a heterodisperse gum matrix comprising a heteropolysaccharide gum and a homopolysaccharide gum capable of cross-linking said heteropolysaccharide in the presence of aqueous solutions, the ratio of said heteropolysaccharide gum to said homopolysaccharide gum being from about 1:3 to about 3:1;

an inert pharmaceutical diluent selected from the group consisting of monosaccharide, a disaccharide, a polyhydric alcohol, and mixtures thereof, the ratio of said inert diluent to said heterodisperse gum matrix being from about 3:7 to about 7:3; and from 4 to about 20 percent by weight of a multi-phasic release promoting agent.

2. The pharmaceutical excipient of claim 1, wherein said heteropolysaccharide gum comprises xanthan gum and said homopolysaccharide gum comprises locust bean gum.

3. The pharmaceutical excipient of claim 1, wherein said inert diluent comprises lactose, dextrose, sucrose, fructose, microcrystalline cellulose, xylitol, sorbitol or mixtures thereof.

4. The pharmaceutical excipient of claim 1, wherein the ratio of said inert diluent to said heterodisperse gum matrix is about 1:1.

5. The pharmaceutical excipient of claim 1, wherein said surfactant comprises sodium lauryl sulfate.

6. The pharmaceutical excipient of claim 1, wherein said surfactant comprises docusate sodium.

7. A controlled release multi-phasic pharmaceutical excipient, comprising:

a heterodisperse gum matrix comprising xanthan gum and locust bean gum in a ratio from about 1:3 to about 3:1;

an inert pharmaceutical diluent selected from the group consisting of monosaccharide, a disaccharide, a polyhydric alcohol, and mixtures thereof, the ratio of said inert diluent to said heterodisperse gum matrix being from about 3:7 to about 7:3; and from 2 to about 20 percent by weight of a multi-phasic release promoting agent selected from the group consisting of sodium lauryl sulfate, docusate sodium, and mixtures thereof.

8. The pharmaceutical excipient of claim 7, wherein said surfactant is selected from the group consisting of pharmaceutically acceptable anionic surfactants, cationic surfactants, amphoteric (amphipathic/amphophilic) surfactants, non-ionic surfactants, and mixtures of any of the foregoing.

9. The pharmaceutical excipient of claim 7, wherein said surfactant is an anionic surfactant selected from the group consisting of monovalent alkyl carboxylates, acyl lactylates, alkyl ether carboxylates, N-acyl sarcosinates, polyvalent alkyl carbonates, N-acyl glutamates, fatty acid-polypeptide condensates, sulfuric acid esters, alkyl sulfates (including sodium lauryl sulfate (SLS)), ethoxylated alkyl sulfates, ester linked sulfonates (including docusate sodium or dioctyl sodium succinate (DSS)), alpha olefin sulfonates, phosphated ethoxylated alcohols, and mixtures of any of the foregoing.

10. The pharmaceutical excipient of claim 7, wherein said surfactant is a cationic surfactant selected from the group consisting of monoalkyl quaternary ammonium salts, dialkyl quaternary ammonium compounds, amidoamines, aminimides, and mixtures of any of the foregoing.

11. The pharmaceutical excipient of claim 7, wherein said surfactant is an amphoteric surfactant selected from the group consisting of N-substituted alkyl amides, N-alkyl betaines, sulfobetaines, N-alkyl β-aminoproprionates, and mixtures of any of the foregoing.

12. The pharmaceutical excipient of claim 7, wherein said surfactant is a non-ionic surfactant selected from the group consisting of ethoxylated alcohols, ethoxylated amides, propoxylated alcohols, ethoxylated/propoxylated block polymers, alkanolamides, amine oxides, fatty acid esters of polyhydric alcohols, ethylene glycol esters, diethylene glycol esters, propylene glycol esters, glyceryl esters, sorbitan esters, sucrose esters, glucose (dextrose) esters, and mixtures of any of the foregoing.

13. The pharmaceutical excipient of claim 7, wherein said surfactant is a wetting agent selected from the group consisting of acacia, benzalkonium chloride, cholesterol, emulsifying wax, docusate sodium, glyceryl monostearate, lanolin alcohols, lecithin, poloxamer, poloxyethylene castor oil derivatives, poloxyethylene sorbitan fatty acid esters, poloxyethylene stearates, sodium lauryl sulfates, sorbitan esters, stearic acid, triethanolamine, and mixtures of any of the foregoing.

14. The pharmaceutical excipient of claim 7, wherein said surfactant is selected from the group consisting of sodium lauryl sulfate/polyethylene glycol (PEG) 6000 and sodium lauryl sulfate/PEG 6000/stearic acid.

15. A method for preparing a controlled release dosage form which exhibits multi-phasic release of a medicament incorporated therein, comprising:

preparing a controlled release multi-phasic excipient by mixing (1) a heteropolysaccharide gum and a homopolysaccharide gum capable of cross-linking said heteropolysaccharide gum in the presence of aqueous solutions, such that the ratio of said heteropolysaccharide gum to said homopolysaccharide gum is from about 1:3 to about 3:1, with (ii) an inert pharmaceutical diluent selected from the group consisting of monosaccharide, a disaccharide, a polyhydric alcohol, and mixtures thereof, the ratio of said inert diluent to said heterodisperse gum matrix being from about 3:7 to about 7:3; and (iii) from 4 to about 20 percent by weight of a multi-phasic release promoting agent;

adding a therapeutically effective amount of a medicament to said controlled release multi-phasic excipient; and tableting said mixture of controlled release multi-phasic excipient and medicament, said multi-phasic release promoting agent being included in an amount sufficient to provide a multi-phasic release of said medicament from said tablet when said tablet is exposed to aqueous fluids.

16. The method of claim 15, wherein said controlled release multi-phasic excipient includes from about 4 to about 10 percent by weight multi-phasic release promoting agent.

17. The method of claim 15, wherein said multi-phasic release promoting agent is selected from the group consisting of anionic surfactants, cationic surfactants, amphoteric surfactants, non-ionic surfactants, and mixtures of any of the foregoing.

18. The method of claim 15, wherein said surfactant is a surfactant selected from the group consisting of sodium lauryl sulfate, docusate sodium, or a mixture of the foregoing.

19. A method for preparing a controlled release dosage form which exhibits multi-phasic release of a medicament incorporated therein, comprising:

preparing a controlled release multi-phasic excipient by mixing (1) xanthan gum and locust bean gum in a ratio of from about 1:3 to about 3:1, with (ii) an inert pharmaceutical diluent selected from the group consisting of monosaccharide, a disaccharide, a polyhydric alcohol, and mixtures thereof, the ratio of said inert diluent to said heterodisperse gum matrix being from about 3:7 to about 7:3; and (iii) from 4 to about 20 percent by weight of a multi-phasic release promoting agent selected from the group consisting of sodium lauryl sulfate, docusate sodium, and mixtures thereof;

adding a therapeutically effective amount of a medicament to said controlled release multi-phasic excipient; and tableting said mixture of controlled release multi-phasic excipient and medicament, said multi-phasic release promoting agent being included in an amount sufficient to provide a multi-phasic release of said medicament from said tablet when said tablet is exposed to aqueous fluids.

* * * * *